United States Patent
Rowe et al.

(10) Patent No.: US 10,023,595 B2
(45) Date of Patent: *Jul. 17, 2018

(54) LIGATED ANIONIC-ELEMENT REAGENT COMPLEXES AS NOVEL REAGENTS FORMED WITH METAL, METALLOID, AND NON-METAL ELEMENTS

(71) Applicants: Toyota Motor Engineering & Manufacturing North America, Inc., Erlanger, KY (US); The University of Manitoba, Winnipeg (CA)

(72) Inventors: Michael Paul Rowe, Pinckney, MI (US); Elizabeth Marie Skoropata, Winnipeg (CA); Johan Alexander van Lierop, Winnipeg (CA)

(73) Assignees: Toyota Motor Engineering & Manufacturing North America, Inc., Plano, TX (US); The University of Manitoba, Winnipeg, Manitoba (CA)

( * ) Notice: Subject to any disclaimer, the term of this patent is extended or adjusted under 35 U.S.C. 154(b) by 115 days.

This patent is subject to a terminal disclaimer.

(21) Appl. No.: 15/176,282

(22) Filed: Jun. 8, 2016

(65) Prior Publication Data

US 2016/0280720 A1 Sep. 29, 2016

Related U.S. Application Data

(63) Continuation-in-part of application No. 14/593,371, filed on Jan. 9, 2015, now Pat. No. 9,546,192.

(60) Provisional application No. 62/319,659, filed on Apr. 7, 2016.

(51) Int. Cl.
   B22F 9/04       (2006.01)
   C07F 7/30       (2006.01)
   B22F 1/00       (2006.01)

(52) U.S. Cl.
   CPC .................. *C07F 7/30* (2013.01); *B22F 9/04* (2013.01); *B22F 1/0018* (2013.01); *B22F 2009/042* (2013.01); *B22F 2009/043* (2013.01)

(58) Field of Classification Search
   CPC ..... B22F 9/04; B22F 1/0018; B22F 2009/042
   See application file for complete search history.

(56) References Cited

U.S. PATENT DOCUMENTS

| | | | |
|---|---|---|---|
| 7,785,392 B2 | 8/2010 | Shim et al. | |
| 7,927,507 B1 | 4/2011 | Li et al. | |
| 8,192,866 B2 | 6/2012 | Golightly et al. | |
| 8,361,651 B2 | 1/2013 | Matsui | |
| 8,372,177 B1 | 2/2013 | Thoma et al. | |
| 8,395,003 B2 | 3/2013 | Leger et al. | |
| 8,980,219 B1 | 3/2015 | Rowe et al. | |
| 9,142,834 B2 | 9/2015 | Mohtadi et al. | |
| 9,546,192 B2* | 1/2017 | Rowe | B22F 1/0003 |
| 9,796,023 B2* | 10/2017 | Rowe | B22F 9/18 |
| 2005/0217427 A1 | 10/2005 | Suthersan et al. | |
| 2006/0177660 A1 | 8/2006 | Kumar et al. | |
| 2009/0029148 A1 | 1/2009 | Hashimoto et al. | |
| 2009/0090214 A1 | 4/2009 | Cheng | |
| 2009/0093553 A1 | 4/2009 | Kleine et al. | |
| 2009/0264277 A1 | 10/2009 | Raj et al. | |
| 2011/0200848 A1 | 8/2011 | Chiang et al. | |
| 2013/0084502 A1 | 4/2013 | Singh et al. | |
| 2013/0133483 A1 | 5/2013 | Yang et al. | |
| 2013/0178357 A1 | 7/2013 | Adzic et al. | |
| 2013/0224603 A1 | 8/2013 | Chen et al. | |
| 2015/0068646 A1 | 3/2015 | Rowe | |
| 2015/0096887 A1 | 4/2015 | McDonald et al. | |
| 2015/0097649 A1 | 4/2015 | Rowe | |
| 2015/0098882 A1 | 4/2015 | Rowe | |
| 2015/0098884 A1 | 4/2015 | Rowe | |
| 2015/0098885 A1 | 4/2015 | Rowe | |
| 2015/0098886 A1 | 4/2015 | Rowe et al. | |
| 2015/0098892 A1 | 4/2015 | Rowe et al. | |
| 2015/0099118 A1 | 4/2015 | Mizuno et al. | |
| 2015/0099135 A1 | 4/2015 | Mohtadi et al. | |
| 2015/0099172 A1 | 4/2015 | Rowe et al. | |
| 2015/0099182 A1 | 4/2015 | Singh et al. | |
| 2015/0099183 A1 | 4/2015 | Singh et al. | |

(Continued)

FOREIGN PATENT DOCUMENTS

| | | |
|---|---|---|
| CN | 102909381 A | 2/2013 |
| DE | 112012001928 T5 | 2/2014 |

(Continued)

OTHER PUBLICATIONS

Harris, "X. Quantitative Measurement of Preferred Orientation in Rolled Uranium Bars", Sep. 1951, pp. 113-123, pp. 113-123 Ser. 7, vol. 43, No. 336.

Imamura et al., "Dehydriding of Sn/MgH2 nanocomposite formed by ball milling of MgH2 with Sn", Int. J. Hydrogen Energy, Jul. 2007, pp. 4191-4194, vol. 32.

Poudyal et al; "Advances in Nanostructured Permanent Magnets Research", Dec. 2012, J. Phys. D: Appl. Phys., pp. 1-23, vol. 46, No. 4.

Schüth et al., "Light Metal Hydrides and Complex Hydrides for Hydrogen Storage", Chem Commun, Sep. 2004, pp. 2249-2258, Issue 20.

(Continued)

*Primary Examiner* — Pancham Bakshi

(74) *Attorney, Agent, or Firm* — Christopher G. Darrow; Darrow Mustafa PC

(57) ABSTRACT

A reagent includes an element, formally in oxidation state zero, in complex with a hydride molecule and an incorporated ligand. The incorporated ligand typically has surface active properties. The reagent, termed a Ligated Anionic Element Reagent Complex, can be useful in synthesis of elemental nanoparticles. A method for synthesizing the aforementioned reagent includes a step of ball-milling a mixture containing an elemental powder, bulk hydride molecule, and bulk ligand. The components of the reagent, once complexed, have altered electronic structure and vibrational modes.

14 Claims, 38 Drawing Sheets

(56) References Cited

U.S. PATENT DOCUMENTS

| | | | |
|---|---|---|---|
| 2016/0199916 A1 | 7/2016 | Rowe et al. | |
| 2016/0200753 A1 | 7/2016 | Rowe et al. | |

FOREIGN PATENT DOCUMENTS

| | | | |
|---|---|---|---|
| JP | 2012038697 A | 2/2012 | |
| JP | 2013073839 A | 4/2013 | |
| JP | 2013131366 A | 7/2013 | |
| WO | 2012007830 A1 | 1/2012 | |
| WO | 2013056185 A1 | 4/2013 | |
| WO | 2013063161 A2 | 5/2013 | |

OTHER PUBLICATIONS

Suzuki et al. "Spin Reorientation Transition and Hard Magnetic Properties of MnBi Intermetallic Compound", Feb. 2012, J. Appl. Phys., pp. 07E303-1-07E303-3, vol. 111.

Varin et al., "The Effects of Ball Milling and Nonmetric Nickel Additive on the Hydrogen Desorption from Lithium Borohydride and Manganese Chloride ($3LiBH_4 + MnCl_2$) Mixture", 2010, Int. J. Hydrogen Energy, pp. 3588-3597, vol. 35.

Wronski et al., "A New Nanonickel Catalyst for Hydrogen Storage in Solid-state Magnesium Hydrides", 2011, Int. J. Hydrogen Energy, pp. 1159-1166, vol. 36.

Yang et al. "Anisotropic Nanocrystalline MnBi with High Coercivity at High Temperature", Aug. 2011, Appl. Phys. Let, vol. 99, Article No. 082505, 4 pages.

Yang et al. "Temperature Dependences of Structure and Coercivity for Melt-spun MnBi Compound", Nov. 2012, J. Magnetism Magnet. Mat, pp. 106-110, vol. 330.

Peng, B. et al., "Functional materials with high-efficiency energy storage and conversion for batteries and fuel cells," Coordination Chemistry Reviews, 253, pp. 2805-2813 (2009).

Sanyal, U. et al., "Bimetallic core-shell nanocomposites using weak reducing agent and their transformation to alloy nanostructures," Dalton Trans., 42, pp. 7147-7157 (2013).

Bhattacharya, V. et al., "Melting of multiphase nano-scaled particles embedded in Al matrix: Case of Pb-Sn and Bi-Sn alloys," Materials Science Engineering A 449-451, pp. 1003-1008 (2007).

\* cited by examiner

LIGATED ANIONIC-ELEMENT REAGENT COMPLEXES AS NOVEL REAGENTS FORMED WITH METAL, METALLOID, AND NON-METAL ELEMENTS

CROSS-REFERENCE TO RELATED APPLICATIONS

This application claims the benefit of U.S. Provisional App. No. 62/319,659, filed Apr. 7, 2016. This application is also a continuation-in-part of U.S. patent application Ser. No. 14/593,371, filed Jan. 9, 2015, now U.S. Pat. No. 9,546,192. Each of the aforementioned documents is incorporated by reference herein in its entirety.

TECHNICAL FIELD

The present disclosure relates in general to a reagent complex having an element in complex with one or more hydride molecules and one or more incorporated ligand molecules. The present disclosure also relates to methods for making the same.

BACKGROUND

The background description provided herein is for the purpose of generally presenting the context of the disclosure. Work of the presently named inventors, to the extent it may be described in this background section, as well as aspects of the description that may not otherwise qualify as prior art at the time of filing, are neither expressly nor impliedly admitted as prior art against the present technology.

Complexes having the general formula $Q^0 \cdot X_y$, where $Q^0$ is a zero-valent element and X is a hydride molecule such as $LiBH_4$, have utility as reagents for the synthesis of elemental nanoparticles, where the nanoparticles include the element, $Q^0$, in elemental form. Modifications to this type of complex, which improve its reactivity and which are applicable across a broad spectrum of elements, $Q^0$, would be desirable.

SUMMARY

The present teachings provide novel reagents and methods for preparing the reagents.

In one aspect, the present teachings provide a reagent. The reagent includes a complex having a formula, $Q^0 \cdot X_y \cdot L_z$. $Q^0$ is an element, formally in oxidation state zero; X is a hydride molecule, L is a ligand, y is an integral or fractional value greater than zero, and z is an integral or fractional value greater than zero.

In another aspect, the present teachings provide a method for synthesizing a reagent. The method includes a step of ball-milling a mixture that includes: an elemental powder comprising an element, formally in oxidation state zero; bulk hydride molecule present at a first molar ratio relative to the elemental powder; and ligand present at a second molar ratio relative to the elemental powder. The ball-milling step produces a complex having a formula, $Q^0 \cdot X_y \cdot L_z$. $Q^0$ is the element; X is the hydride molecule, L is the ligand, y corresponds to the first molar ratio, and z corresponds to the second molar ratio.

BRIEF DESCRIPTION OF THE DRAWINGS

Various aspects and advantages of the disclosure will become apparent and more readily appreciated from the following description of the embodiments taken in conjunction with the accompanying drawings, of which.

DETAILED DESCRIPTION

Figure 1A:
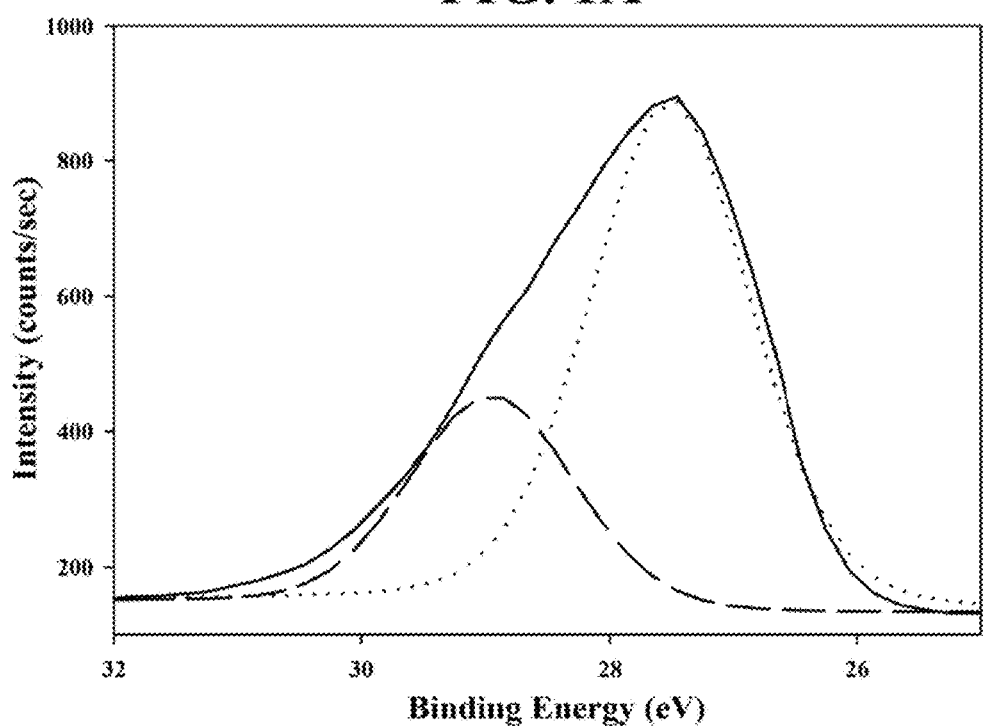
FIG. 1A is a germanium-region XPS of a Ligated Anionic Element Reagent Complex (LAERC) having the formula $Ge(LiBH_4)_2(undecyl\ cyanide)_3$.
Figure 1B:
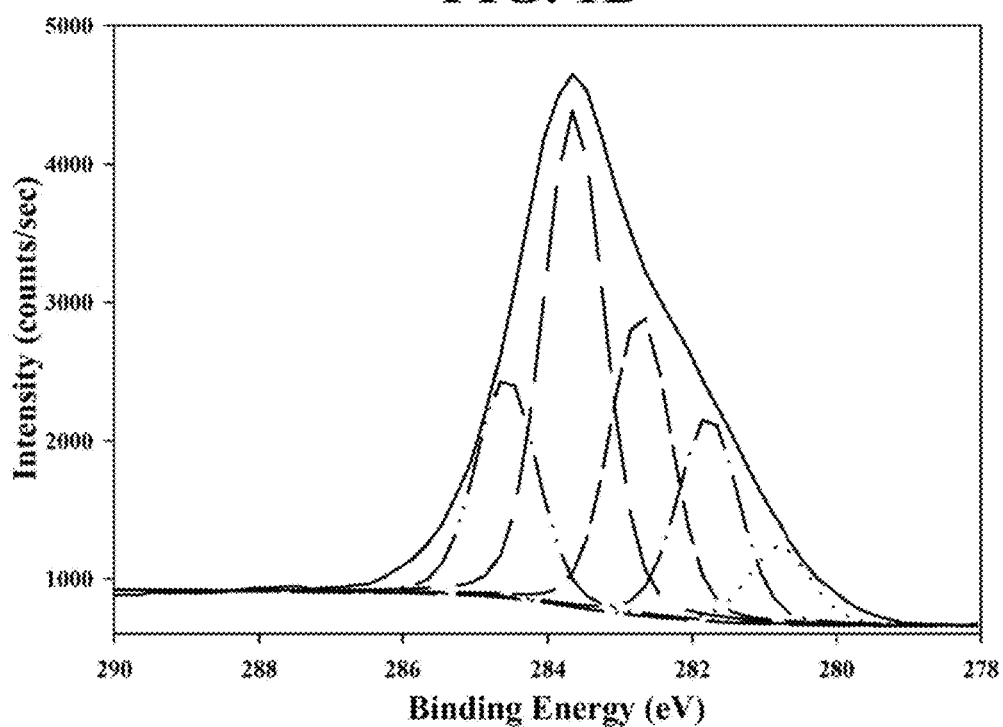
FIG. 1B is a carbon-region XPS of the LAERC of FIG. 1A.
Figure 1C:
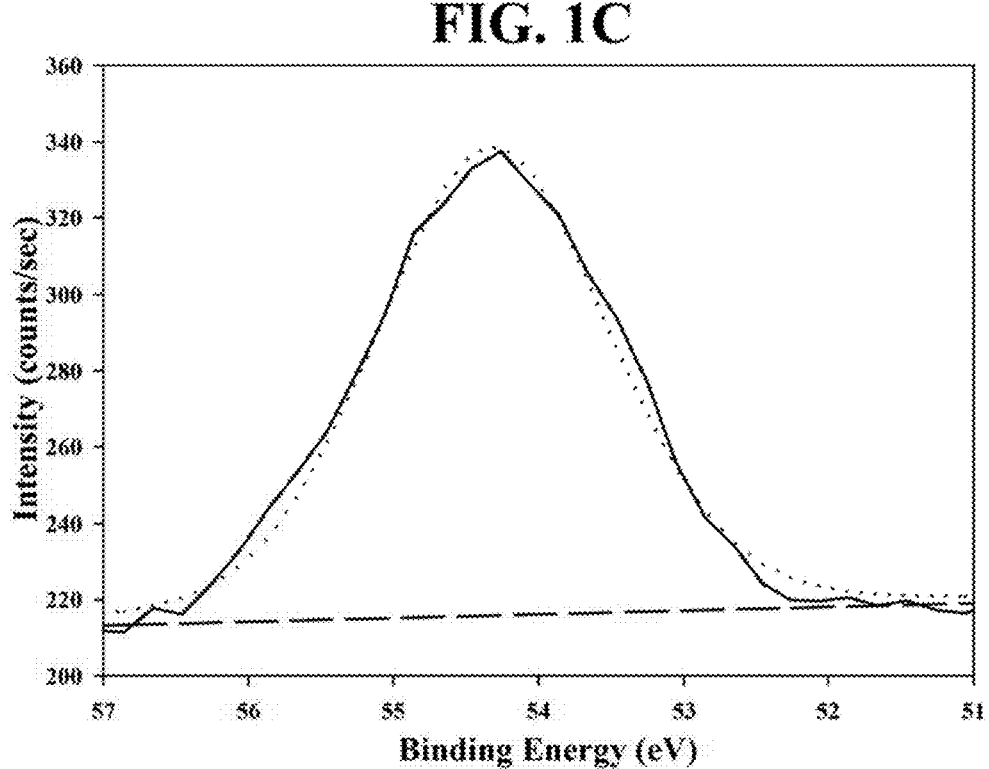
FIG. 1C is a lithium-region XPS of the LAERC of FIG. 1A.
Figure 1D:
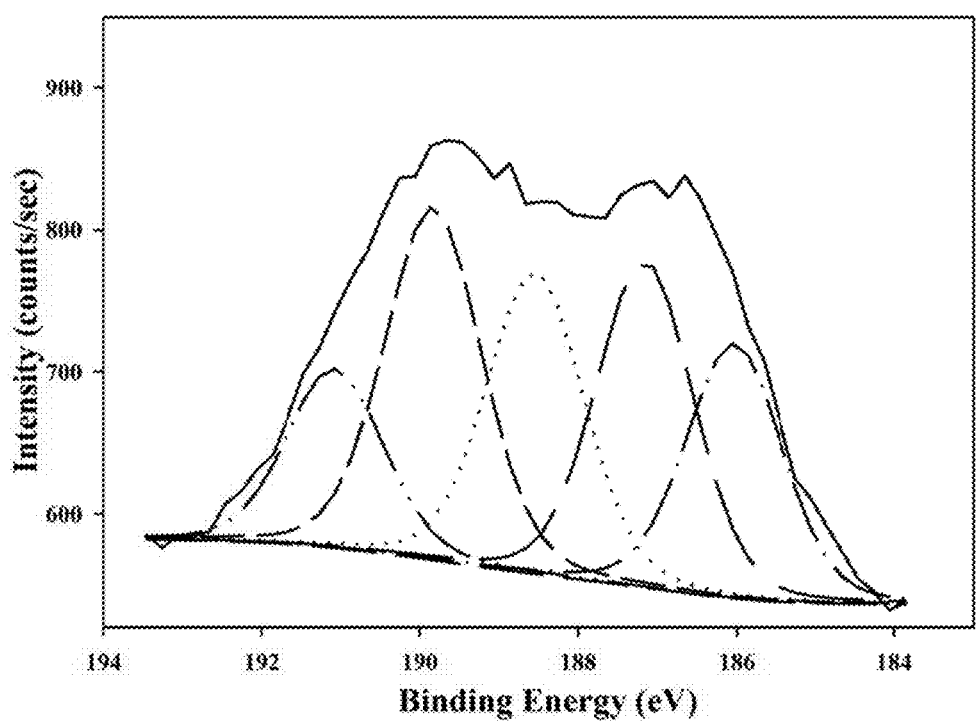
FIG. 1D is a boron-region XPS of the LAERC of FIG. 1A.
Figure 1E:
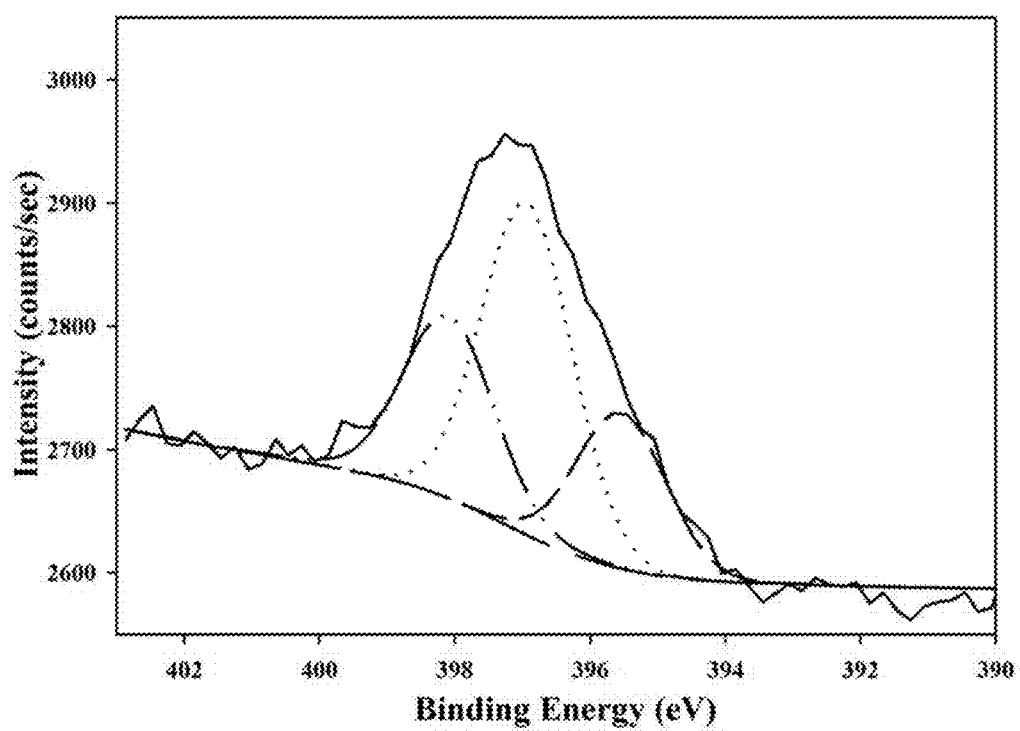
FIG. 1E is a nitrogen-region XPS of the LAERC of FIG. 1A.

The present teachings provide reagents useful in the synthesis of elemental nanoparticles. In particular, the reagents can be employed to easily and reproducibly prepare nanoparticles composed of metal, metalloid, non-metal, or combinations thereof. The present teachings also provide methods for producing the aforementioned reagents. The methods are robust, relatively inexpensive, and amenable to large-scale production.

The reagents generally consist of a supramolecular complex having an element, formally in oxidation state zero, a hydride molecule, and an incorporated ligand. The element can be any element from Groups 2-16 and the incorporated ligand is typically a surface active molecule. The methods include ball-milling a mixture that includes powders of the element, the hydride molecule, and the ligand.

Thus, a reagent is disclosed, comprising a complex according to Formula I:

$$Q^0 \cdot X_y \cdot L_z \qquad\qquad I,$$

wherein $Q^0$ is an element, formally in oxidation state zero, X is a hydride molecule, L is an incorporated ligand, y is an integral or fractional value greater than zero, and z is an integral or fractional value greater than zero. The complex according to Formula I is alternatively referred to below as a "ligated reagent complex" or a LAERC (Ligated Anionic Element Reagent Complex).

The term "element", as used herein, refers generally to elements of Groups 2-16. The description that the element is formally in oxidation state zero indicates, at least, that it is in elemental form, having no formal positive or negative charge. Atoms of the element, formally in oxidation state zero, will alternatively be referred to herein as "elemental atoms".

In another aspect, the term "element" can refer to at least one of a metal, a metalloid, and a non-metal. In this usage, a non-metal, for example, refers to any of carbon, phosphorous, sulfur, and selenium; a metalloid, for example, refers to any of boron, silicon, germanium, arsenic, antimony, tellurium, and polonium; and a metal, for example, refers to any element of Groups 2-15 exclusive of metalloids and non-metals. In some instances, a metal can include a lanthanide. In some examples, $Q^0$ is an element and that is selected from any of Groups 2, 6, 7, 8, 9, 11, 13, 14, and 16.

In some specific examples, $Q^0$ is any of boron, carbon, magnesium, titanium, manganese, iron, cobalt, copper, germanium, selenium, molybdenum, tin, and tungsten. It is to be understood that in some circumstances, $Q^0$ can include more than one element. For example, $Q^0$ according to Formula I could include a combination of elemental tin and copper, both formally in oxidation state zero.

As used herein, the term "hydride molecule" refers generally to any molecule capable to function as a donor of hydrogen anion, or hydride anion. In some instances, a hydride molecule as referenced herein can be a binary metal hydride or "salt hydride" (e.g. NaH, or $MgH_2$), a binary metalloid hydride (e.g. $BH_3$), a complex metal hydride (e.g. $LiAlH_4$), or a complex metalloid hydride (e.g. $LiBH_4$ or $Li(CH_3CH_2)_3BH$). In some examples the hydride will be $LiBH_4$. The term hydride as described above can in some variations include a corresponding deuteride or tritide.

The term "ligand", as used herein, refers to a molecule suitable for incorporation into a complex according to Formula I, and the phrase "incorporated ligand" refers to a ligand that has been so incorporated. An incorporated ligand may serve to improve the reactive characteristics of the reagent (relative to an otherwise identical reagent having no incorporated ligand). A ligand, incorporated or free, will typically be a molecule having significant surface active properties, i.e. a surfactant.

Non-limiting examples of suitable ligands can include nonionic, cationic, anionic, amphoteric, zwitterionic, monodentate, multidentate, chelating and polymeric ligands and combinations thereof. Such ligands typically have a lipophilic moiety that is hydrocarbon based, organosilane based, or fluorocarbon based. Without implying limitation, examples of types of ligands which can be suitable include alkyl sulfates and sulfonates, petroleum and lignin sulfonates, phosphate esters, sulfosuccinate esters, carboxylates, alcohols, ethoxylated alcohols and alkylphenols, fatty acid esters, ethoxylated acids, alkanolamides, ethoxylated amines, amine oxides, nitriles, alkyl amines, quaternary ammonium salts, carboxybetaines, sulfobetaines, or polymeric ligands. In some particular implementations, a ligand can be at least one of a nitrile, an amine, and a carboxylate. In some specific examples, a ligand can be undecyl cyanide, $CH_3(CH_2)_{10}CN$, alternatively referred to as dodecane nitrile.

The value y according to Formula I defines the stoichiometry of hydride molecules to atoms of the element within the complex. The value of y can include any integral or fractional value greater than zero. In some particular instances, y can equal one, two, three, or four.

The value z according to Formula I defines the stoichiometry of incorporated ligand molecules to atoms of the element within the complex. The value of z can include any integral or fractional value greater than zero. In some instances, z can equal one, two, three, or four. The values of y and z can be equal to one another or can differ from one another, in various implementations. In some specific instances, the values of y and z will be equal to one another.

As noted, the LAERCs of the present disclosure can have improved reactivity in comparison to previously disclosed non-ligated reagent complexes (AERCs) having the formula $Q^0 \cdot X_y$, where $Q^0$, X, and y are as described above. Without being bound to any particular theory, it is believed that inclusion of the incorporated ligand may provide a smaller, more uniform, or otherwise more favorable particle size or form of the reagent.

The LAERCs of the present disclosure can have any supramolecular structure, or no supramolecular structure. For example, the complex can exist as a supramolecular cluster of many elemental atoms interspersed with hydride molecules and/or incorporated ligand molecules. The complex could exist as a cluster of elemental atoms in which the cluster is surface-coated with hydride molecules and/or incorporated ligand molecules. The ligated reagent complex could exist as individual elemental atoms having little to no molecular association with one another, but each being associated with hydride molecules and incorporated ligand molecules according to Formula I. Any of these microscopic structures, or any other structure consistent with Formula I, is intended to be within the scope of the present disclosure.

Additionally disclosed is a method for synthesizing a reagent, or LAERC, of the type described above. The method includes a step of ball-milling a mixture that includes: (i) a powder of an element, the element being formally in oxidation state zero, (ii) a bulk preparation of a hydride molecule, and (iii) a bulk preparation of a ligand.

As used in relation to the disclosed method, the powder of an element can alternatively be referred to as an "elemental powder". The terms "hydride molecule" and "ligand" are as defined above, and bulk preparations thereof, or any other bulk forms that are readily reducible to powder, for example by ball-milling. An example of such another bulk form can be a compacted granular form. The bulk preparation of a hydride molecule and the bulk preparation of a ligand can be referred to alternatively as "bulk hydride molecule" and "bulk ligand" respectively. It will be appreciated that the elemental powder, bulk hydride molecule, and/or bulk ligand will not necessarily be 100% pure, but should generally consist predominantly of the element, the hydride molecule, and the ligand, respectively.

In some instances, the ball-milling step can be performed in an oxygen-free environment, in an anhydrous environment, or in an environment that is oxygen-free and anhydrous, such as under argon or under vacuum. An oxygen-free and/or anhydrous environment can potentially limit undesired oxidation of the resulting ligated reagent complex.

The ball-milling step of the present method will generally produce a complex according to Formula I, as described above, and the element, $Q^0$, as present in the complex will generally correspond to the element as present in the elemental powder. The mixture that is ball-milled in the ball-milling step can include any non-zero molar ratio of hydride molecules contained in the bulk hydride molecule to elemental atoms contained in the elemental powder. It will be understood that the value y in Formula I for the complex produced by the ball-milling step will generally reflect this molar ratio. For example, if the mixture to be ball-milled includes two equivalents of hydride molecule and one equivalent of elemental atoms, then the value y, according to Formula I, for the resulting complex will be two.

Similarly, the mixture that is ball-milled in the ball-milling step can include any non-zero molar ratio of ligand molecules contained in the bulk ligand to elemental atoms contained in the elemental powder. It will be understood that the value of z in Formula I for the complex produced by the ball-milling step will generally reflect this molar ratio. For example, if the mixture to be ball-milled includes two equivalents of ligand molecule and one equivalent of elemental atoms, then the value z, according to Formula I, for the resulting complex will be two. Without being bound by any particular theory, it is believed that inclusion of bulk ligand can, among other effects, function to ablate or otherwise assist in decreasing the particle size of the elemental powder and/or of the formative complex during ball-milling.

The present disclosure is further illustrated with respect to the following examples. It needs to be understood that these examples are provided to illustrate specific embodiments of the present disclosure and should not be construed as limiting the scope of the present disclosure.

Examples. LAERC Synthesis

One molar equivalent of germanium powder (Example 1) is combined with two molar equivalents of lithium borohydride and three molar equivalents of undecyl cyanide to produce a mixture. The mixture is added to Teflon lined ball mill jar under argon, with ceramic balls. The LAERC is then formed mechanochemically by milling in a planetary ball mill, at 100 to 300 rpm (depending on hardness of metal, metalloid and/or non-metal elemental powder), for 4 hours. The same procedure is repeated with elemental powders of carbon (Example 2), boron (Example 3), magnesium (Example 4), titanium (Example 5), manganese (Example 6), iron (Example 7), cobalt (Example 8), copper (Example 9), molybdenum (Example 10), tin (Example 11), tungsten (Example 12), selenium (Example 13), and successful LAERC formation with each element is confirmed by XPS and FT-IR. The above-referenced XPS and FTIR spectra are shown in FIGS. 1A-13E, commensurate with Examples 1-13, respectively.

In one Example, bulk germanium powder can be combined with lithium borohydride and with undecyl cyanide in a 1:3:3 molar ratio, to produce a mixture. The mixture can then be ball-milled in an inert environment for four hours. The resulting product is the complex $Ge^0 \cdot Li(BH_4)_3 \cdot [CH_3(CH_2)_{10}CN]_3$ (referred to as "Ge-LAERC"). FIGS. 1A-E show XPS of the Ge-LAERC in the binding energy regions corresponding to valence electrons of germanium, carbon, lithium, boron, and nitrogen, respectively. Such XPS regions are referred to as the germanium-region, carbon-region, lithium-region, boron-region, and nitrogen-region, here and above. In all of FIGS. 1A-E, the solid line, generally having the highest intensity values, represents acquired data, while the various dashed and dotted lines, generally having lower intensity values and each having a single Gaussian peak, show computationally deconvoluted component peaks.

It has been observed that formation of Anionic Element Reagent Complexes (AERCs), lacking an incorporated ligand, results in significant XPS shifts of electrons associated with the elemental component of the reagent. Such shifts virtually always include, and are often dominated by, shifts to lower binding energy. Without being bound to any particular theory, it is believed that these shifts may be indicative of electronic interaction between the electron rich hydride molecule and the element. Such interaction may involve a degree of electron density sharing, giving the elemental component an anionic character.

Referring now particularly to FIG. 1A the germanium-region XPS of Ge-LAERC shows a major peak centered at 27.5 eV. This represents a shift of −1.5 eV relative to elemental Germanium which has a major peak centered at 29.0 eV. This result is indicative of successful formation of the LAERC. It is to be noted that XPS in the lithium and boron-regions for Ge-LAERC also differ from XPS of free lithium borohydride, suggesting that complexation affects the electronic structure of the hydride molecule component of the reagent, as well. Comparable results are obtained with a wide variety of elements, including metals, metalloids, and non-metals (see Examples).

Figure 2A:
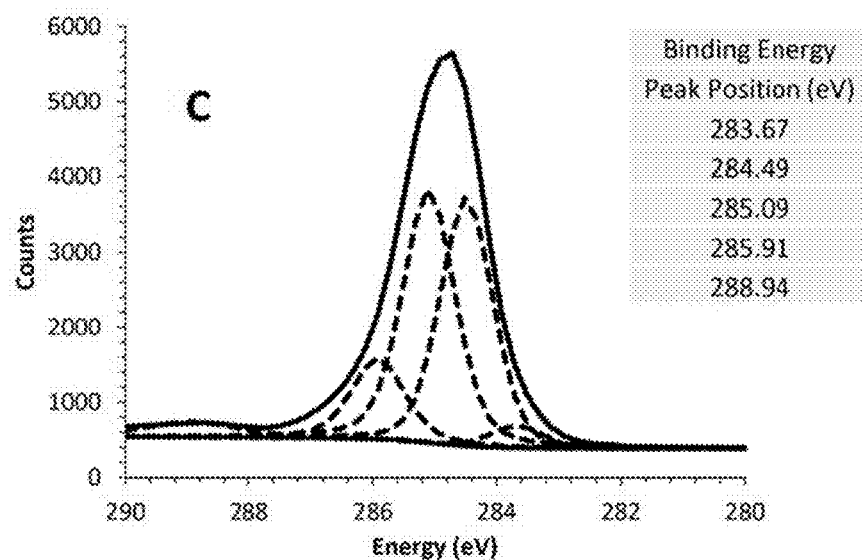
FIG. 2A is a carbon-region XPS of a LAERC having the formula $C(LiBH_4)_2(undecyl\ cyanide)_3$.
Figure 2B:
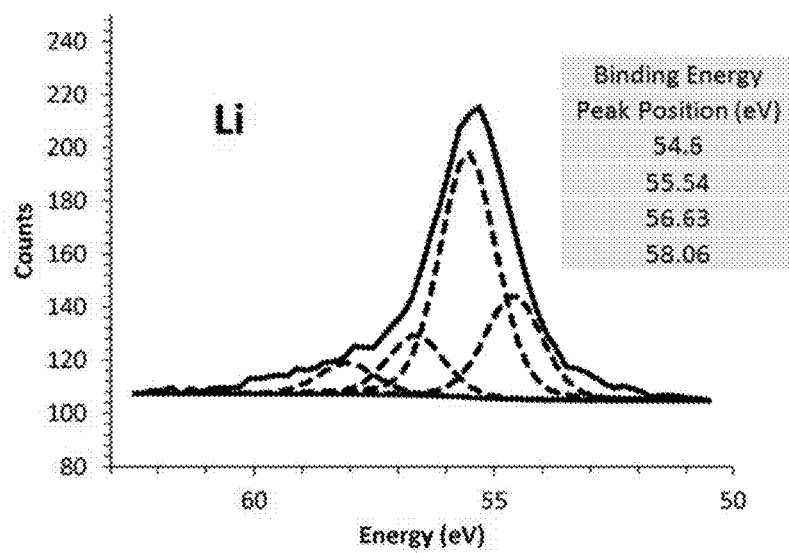
FIG. 2B is a lithium-region XPS of the LAERC of FIG. 2A.
Figure 2C:
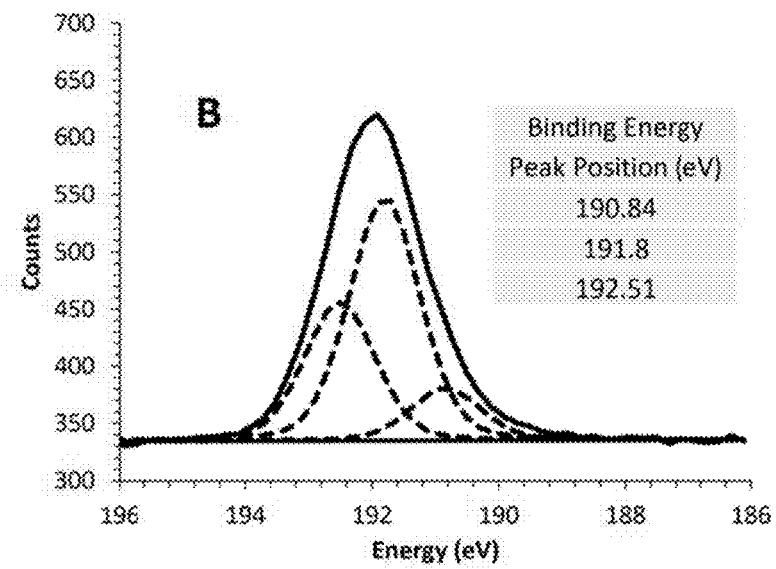
FIG. 2C is a boron-region XPS of the LAERC of FIG. 2A.
Figure 2D:
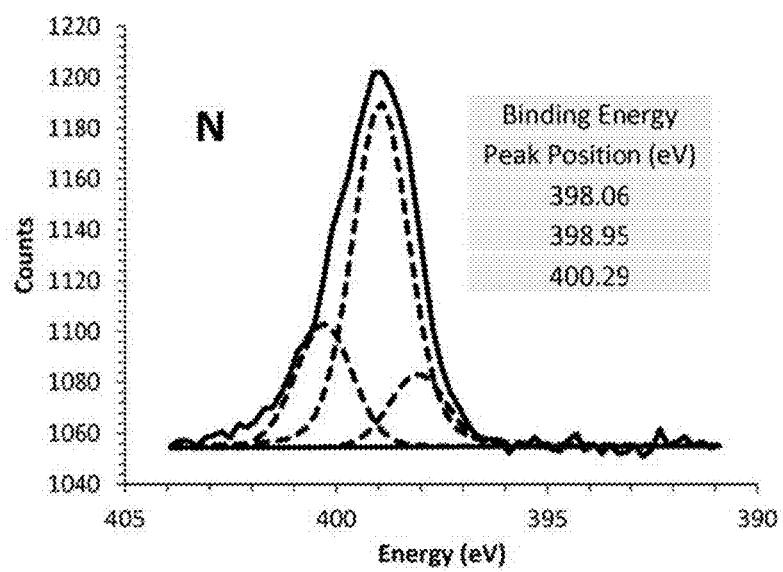
FIG. 2D is a nitrogen-region XPS of the LAERC of FIG. 2A.
Figure 2E:
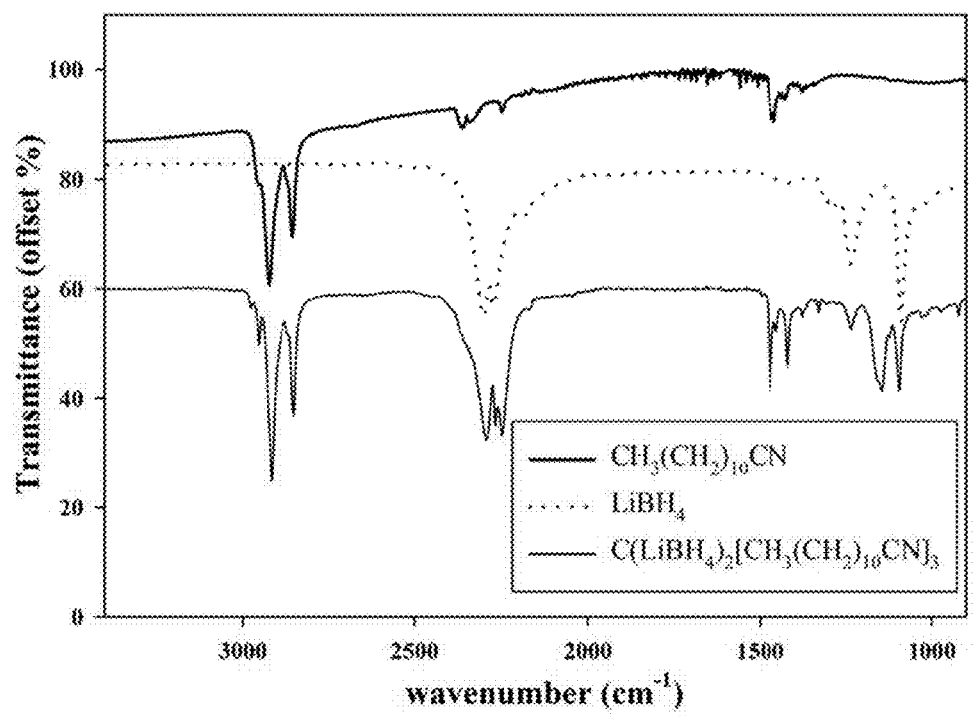
FIG. 2E is an offset overlay of Fourier-transform infrared spectra (FTIR) of undecyl cyanide, lithium borohydride, and the LAERC of FIG. 2A.
Figure 3A:
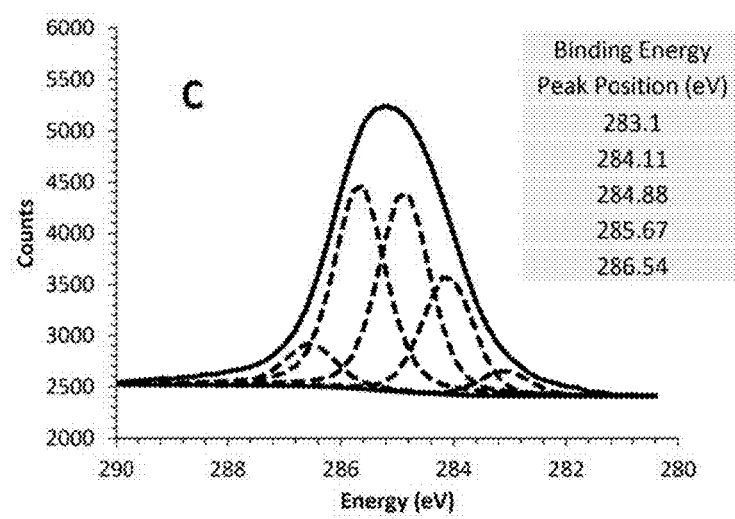
FIG. 3A is a carbon-region XPS of a LAERC having the formula $B(LiBH_4)_2(undecyl\ cyanide)_3$.
Figure 3B:
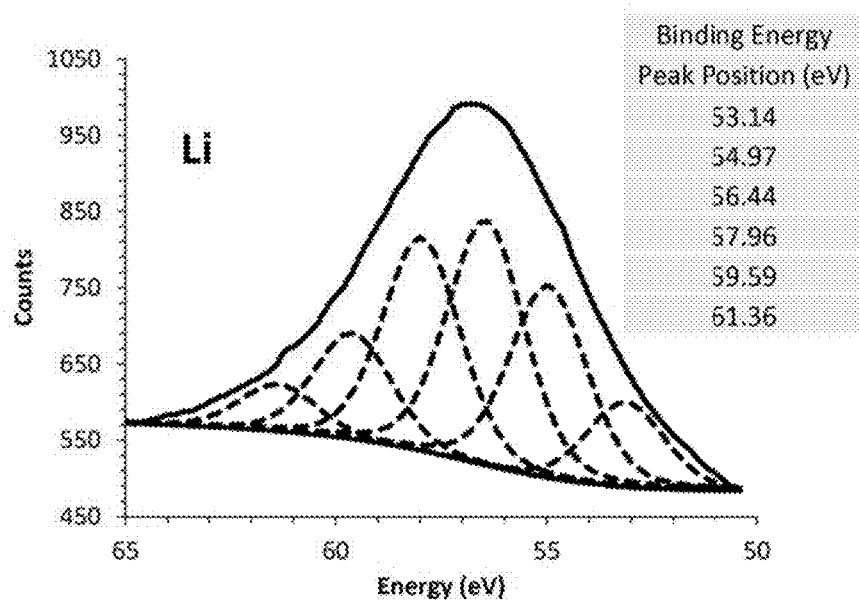
FIG. 3B is a lithium-region XPS of the LAERC of FIG. 3A.
Figure 3C:
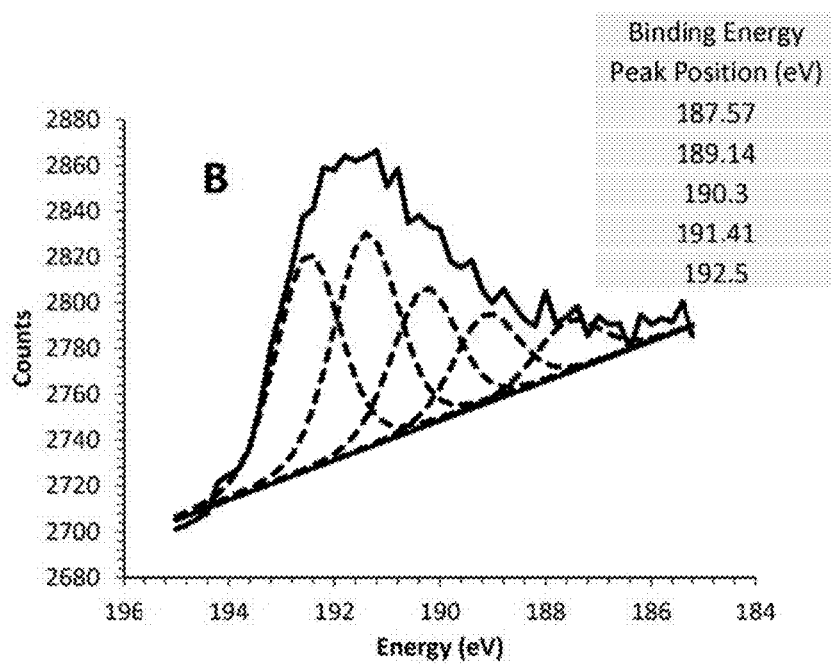
FIG. 3C is a boron-region XPS of the LAERC of FIG. 3A.
Figure 3D:
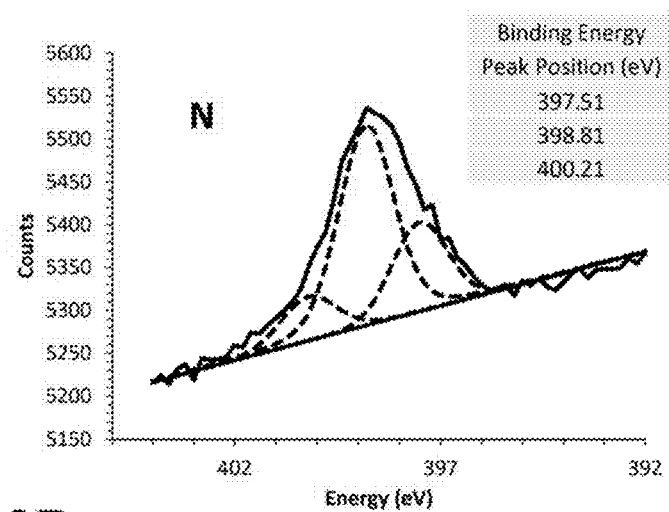
FIG. 3D is a nitrogen-region XPS of the LAERC of FIG. 3A.
Figure 3E:
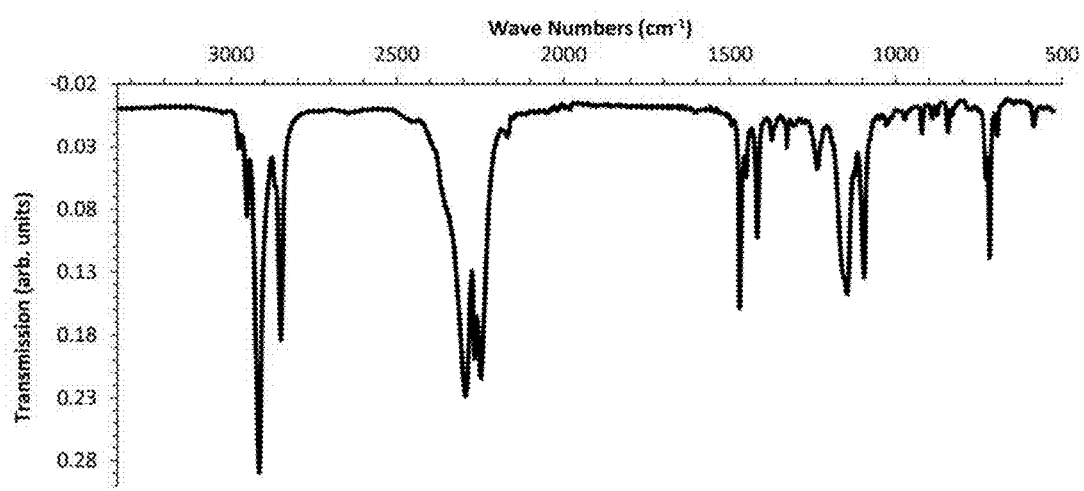
FIG. 3E is an FTIR of the LAERC of FIG. 3A.
Figure 4A:
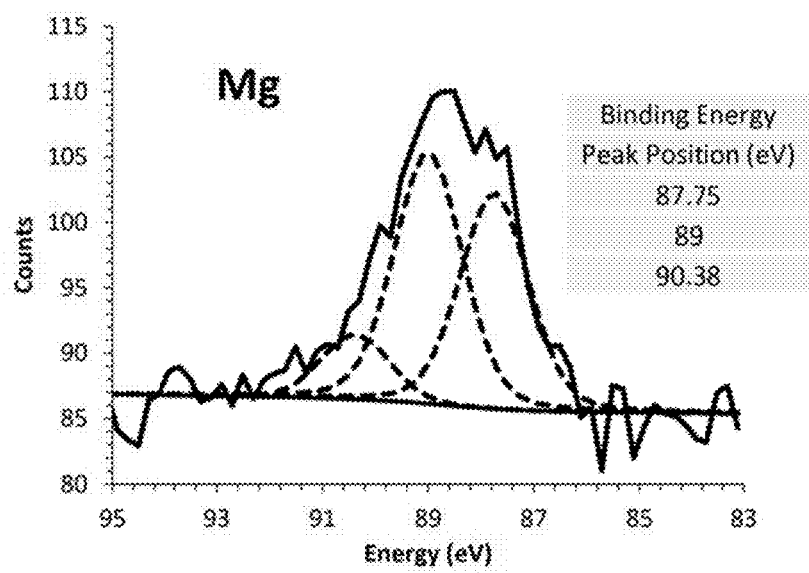
FIG. 4A is a magnesium-region XPS of a LAERC having the formula $Mg(LiBH_4)_2(undecyl\ cyanide)_3$.
Figure 4B:
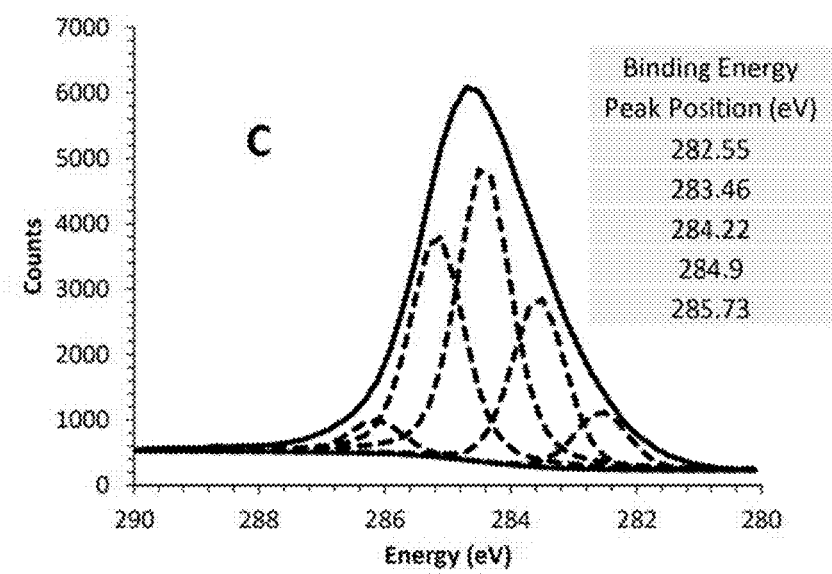
FIG. 4B is a carbon-region XPS of the LAERC of FIG. 4A.
Figure 4C:
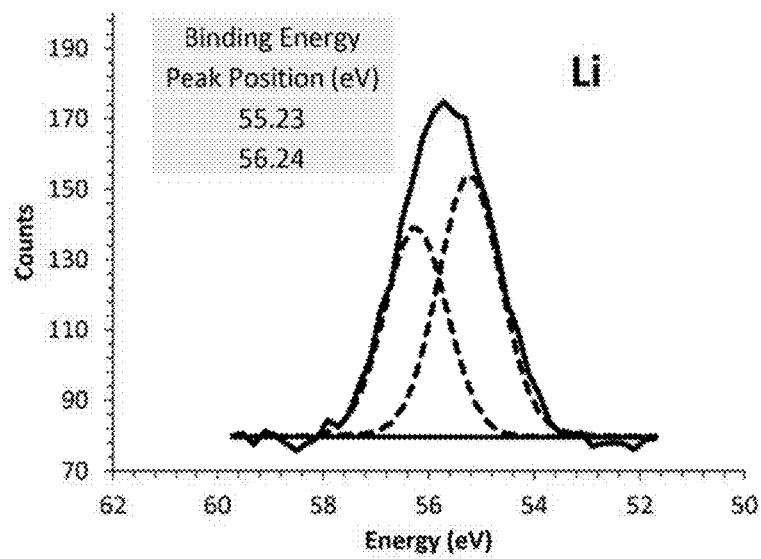
FIG. 4C is a lithium-region XPS of the LAERC of FIG. 4A.
Figure 4D:
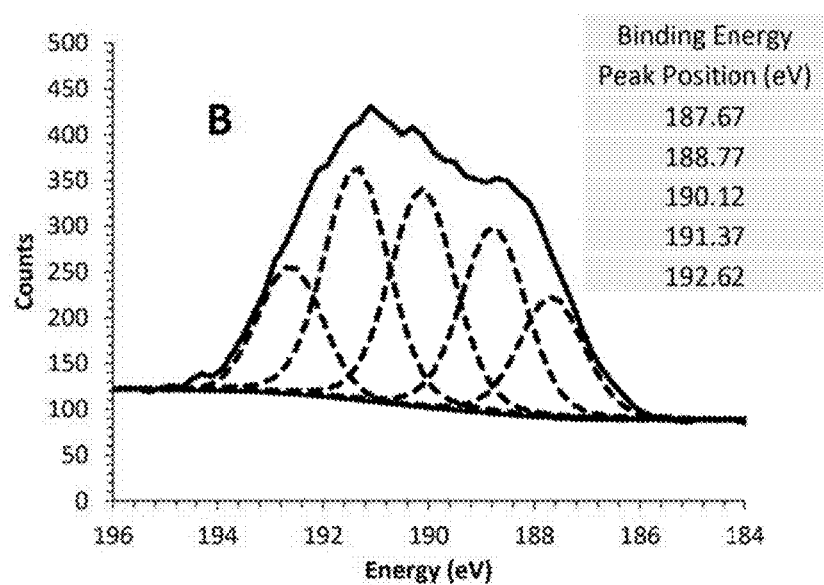
FIG. 4D is a boron-region XPS of the LAERC of FIG. 4A.
Figure 4E:
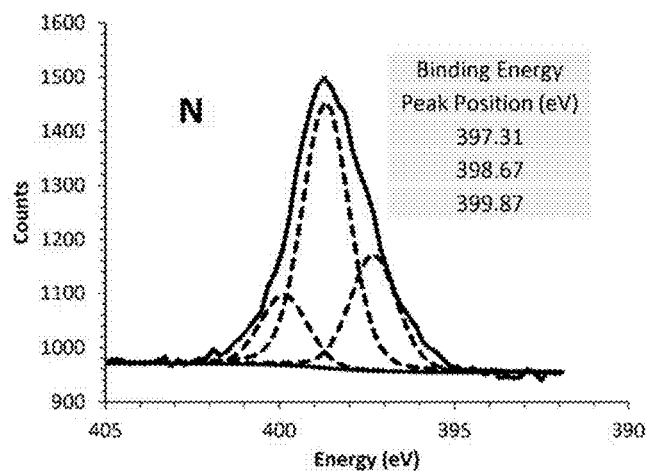
FIG. 4E is a nitrogen-region XPS of the LAERC of FIG. 4A.
Figure 4F:
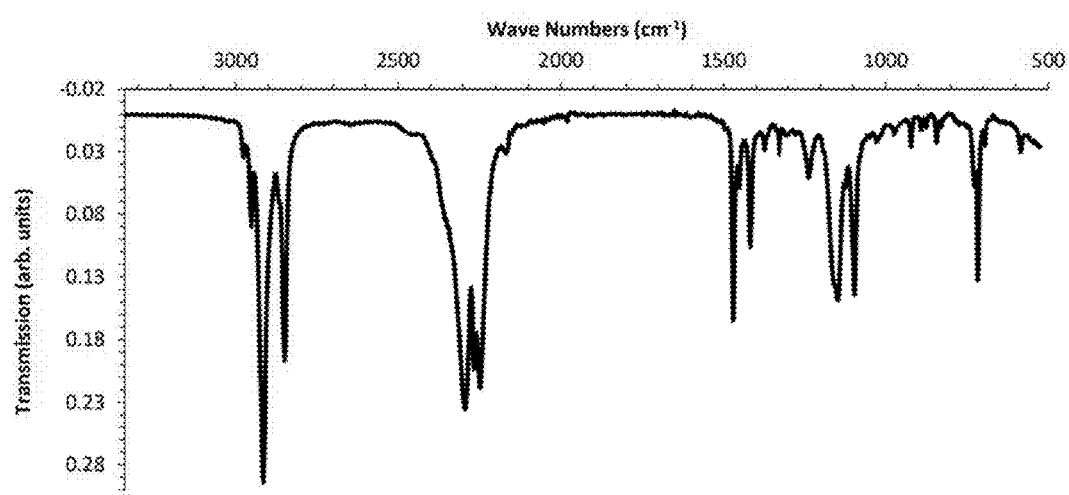
FIG. 4F is an FTIR of the LAERC of FIG. 4A.
Figure 5A:
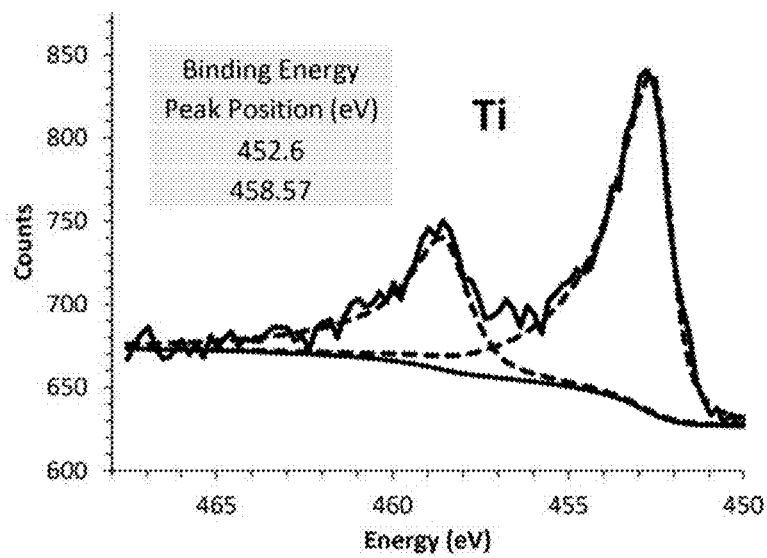
FIG. 5A is a titanium-region XPS of a LAERC having the formula $Ti(LiBH_4)_2(undecyl\ cyanide)_3$.
Figure 5B:
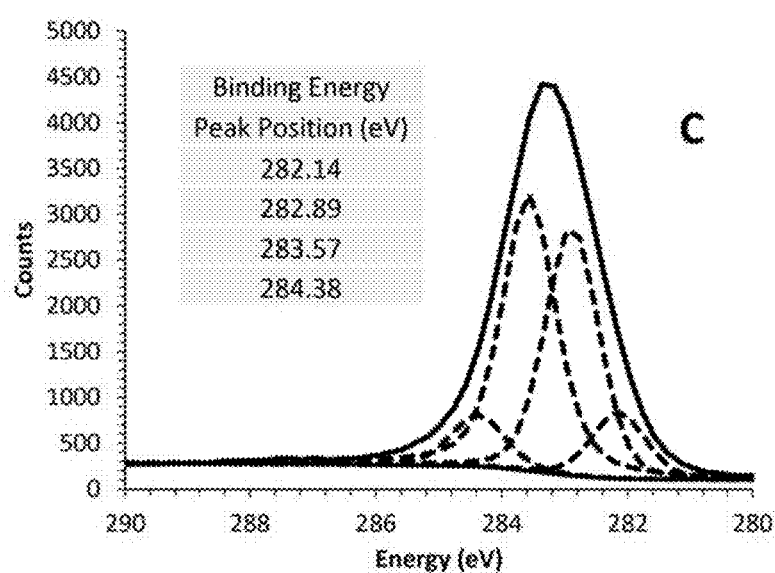
FIG. 5B is a carbon-region XPS of the LAERC of FIG. 5A.
Figure 5C:
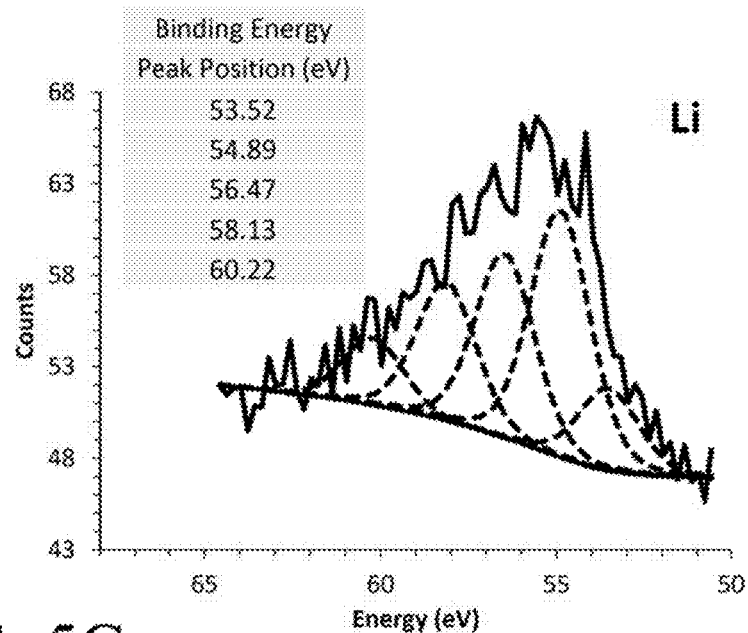
FIG. 5C is a lithium-region XPS of the LAERC of FIG. 5A.
Figure 5D:
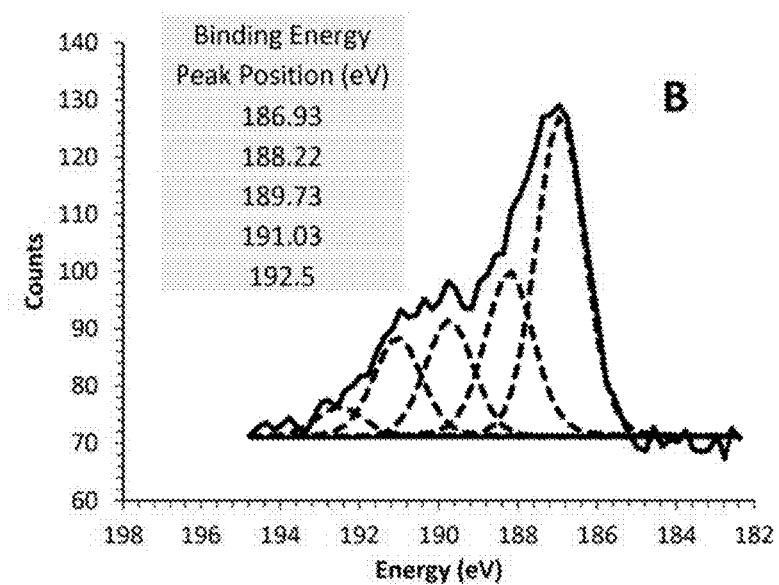
FIG. 5D is a boron-region XPS of the LAERC of FIG. 5A.
Figure 5E:
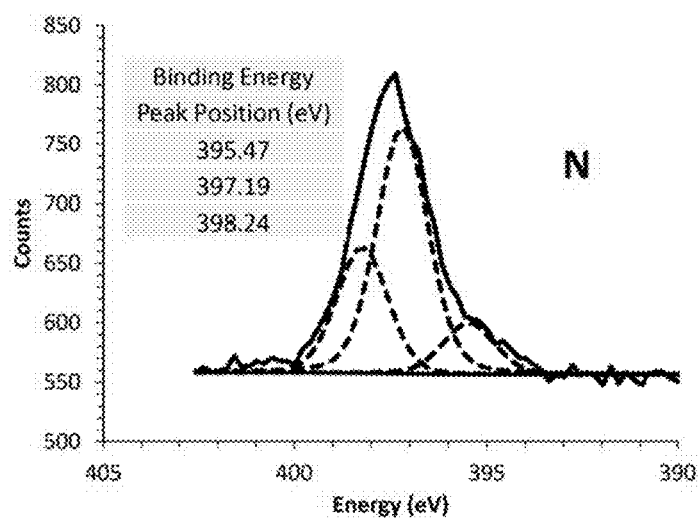
FIG. 5E is a nitrogen-region XPS of the LAERC of FIG. 5A.
Figure 5F:
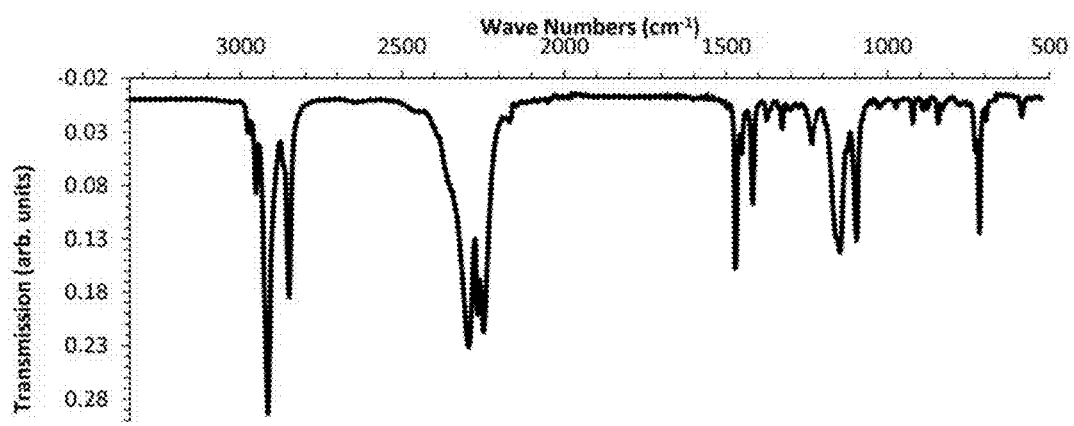
FIG. 5F is an FTIR of the LAERC of FIG. 5A.
Figure 6A:
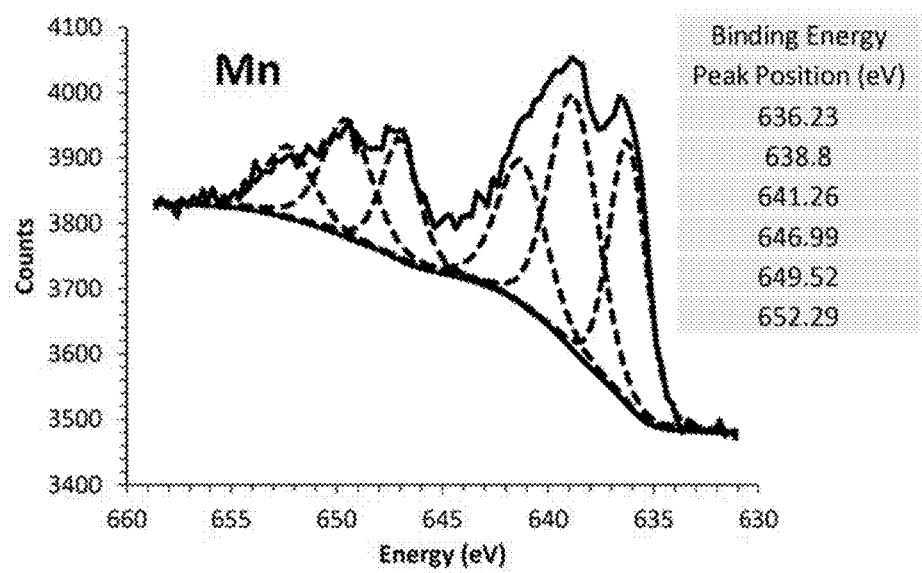
FIG. 6A is a manganese-region XPS of a LAERC having the formula $Mn(LiBH_4)_2(undecyl\ cyanide)_3$.
Figure 6B:
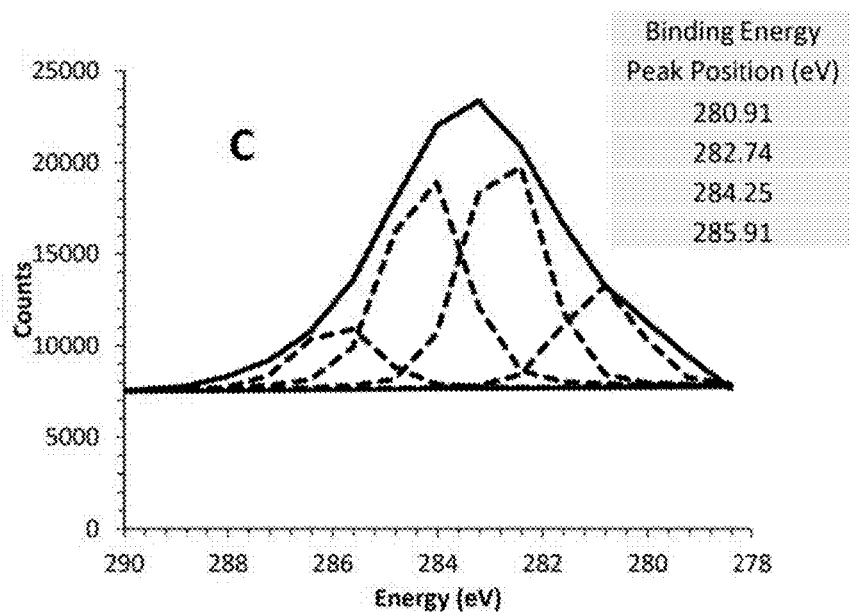
FIG. 6B is a carbon-region XPS of the LAERC of FIG. 6A.
Figure 6C:
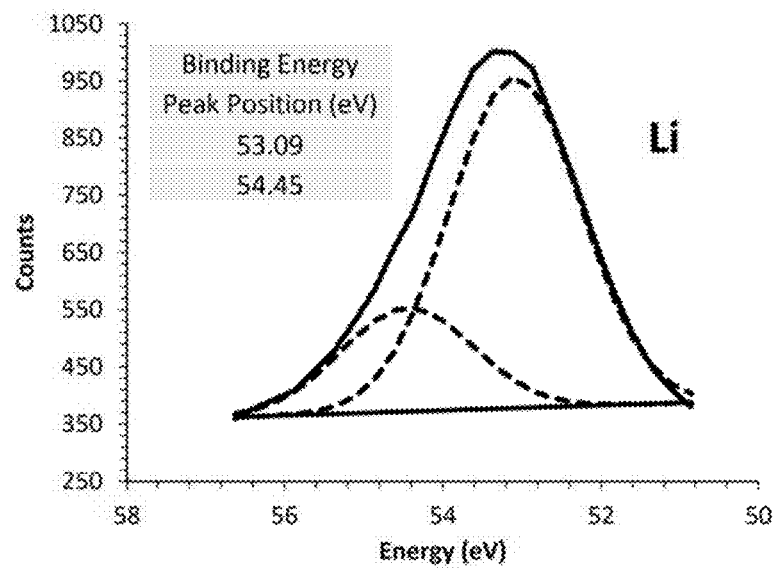
FIG. 6C is a lithium-region XPS of the LAERC of FIG. 6A.
Figure 6D:
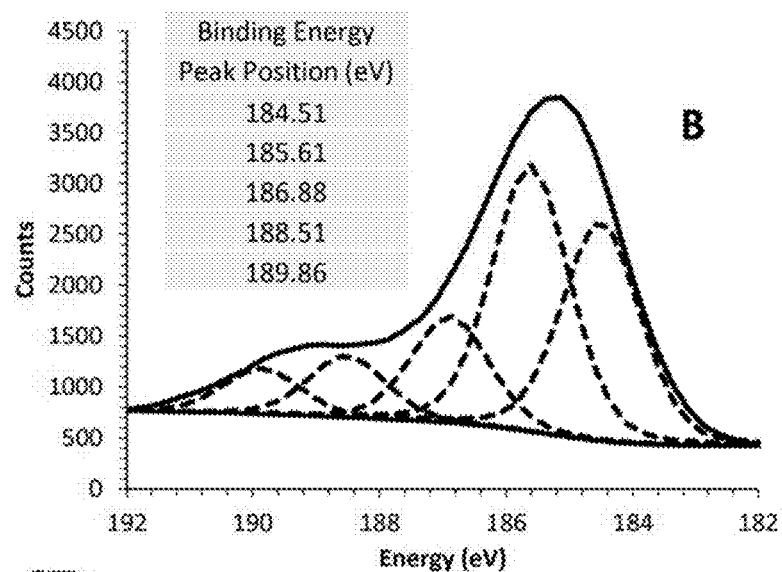
FIG. 6D is a boron-region XPS of the LAERC of FIG. 6A.
Figure 6E:
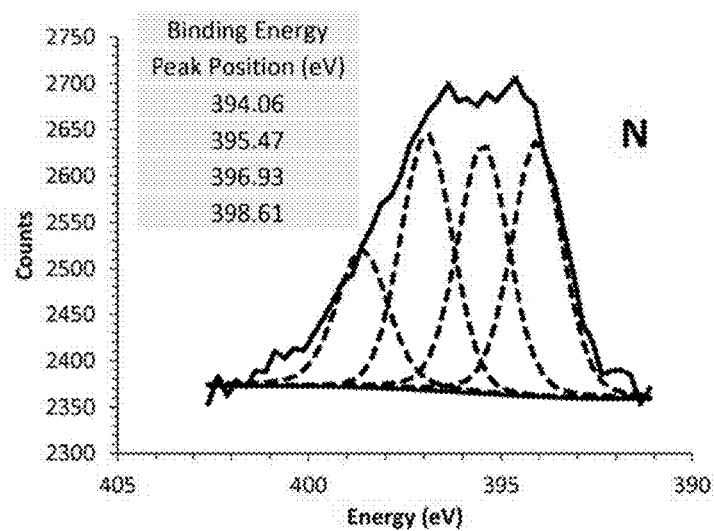
FIG. 6E is a nitrogen-region XPS of the LAERC of FIG. 6A.
Figure 6F:
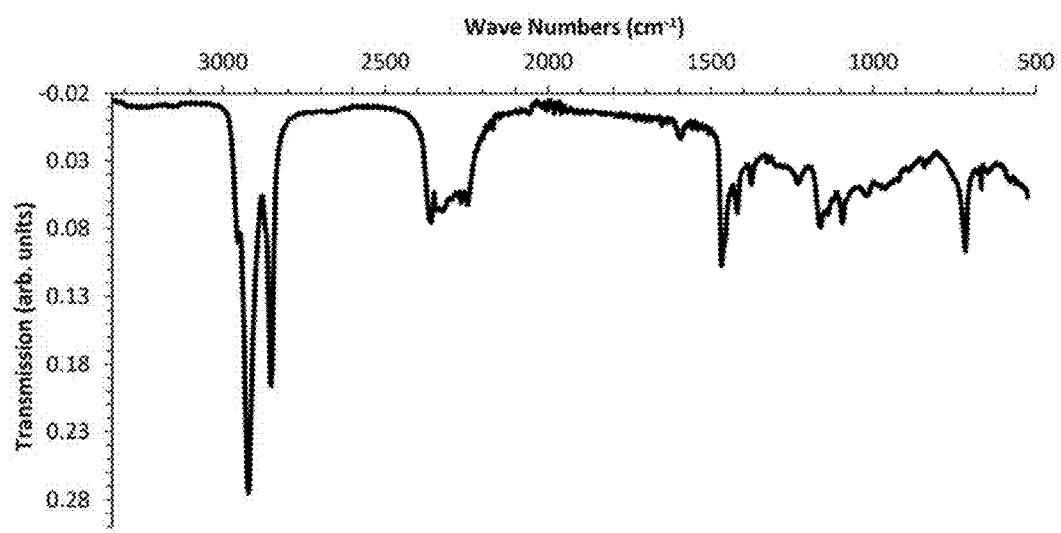
FIG. 6F is an FTIR of the LAERC of FIG. 6A.
Figure 7A:
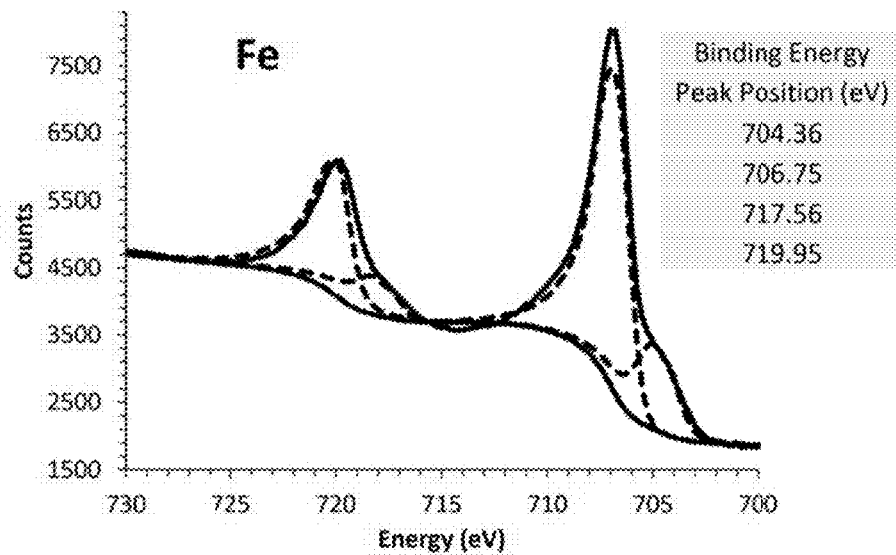
FIG. 7A is an iron-region XPS of a LAERC having the formula $Fe(LiBH_4)_2(undecyl\ cyanide)_3$.
Figure 7B:
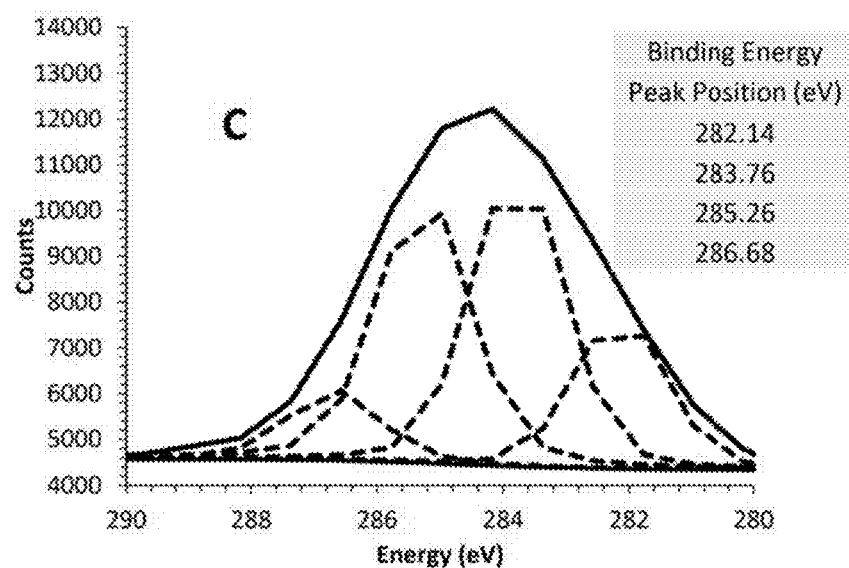
FIG. 7B is a carbon-region XPS of the LAERC of FIG. 7A.
Figure 7C:
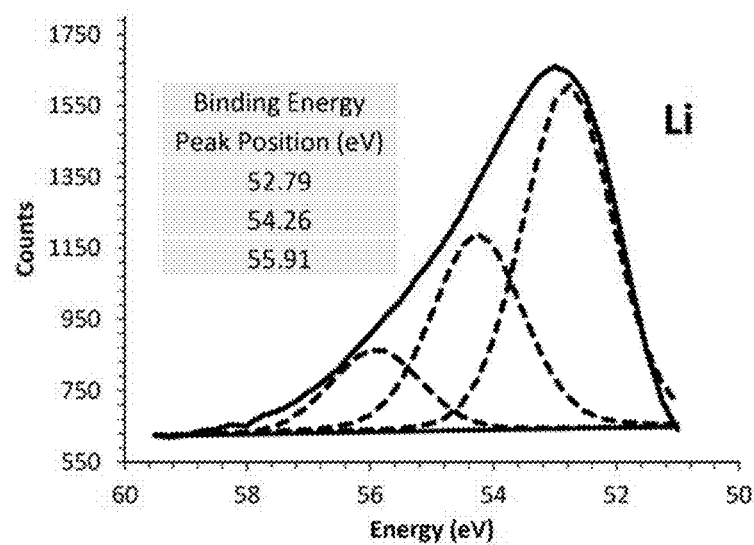
FIG. 7C is a lithium-region XPS of the LAERC of FIG. 7A.
Figure 7D:
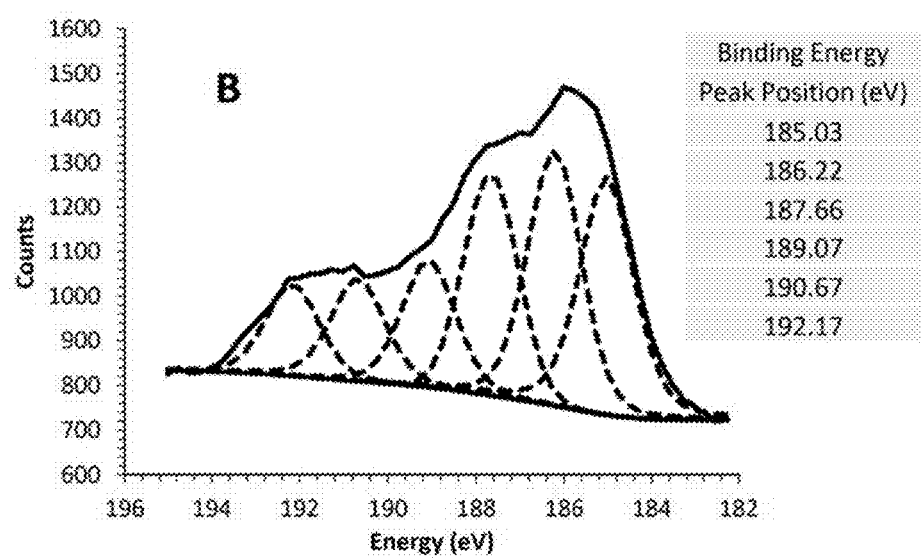
FIG. 7D is a boron-region XPS of the LAERC of FIG. 7A.
Figure 7E:
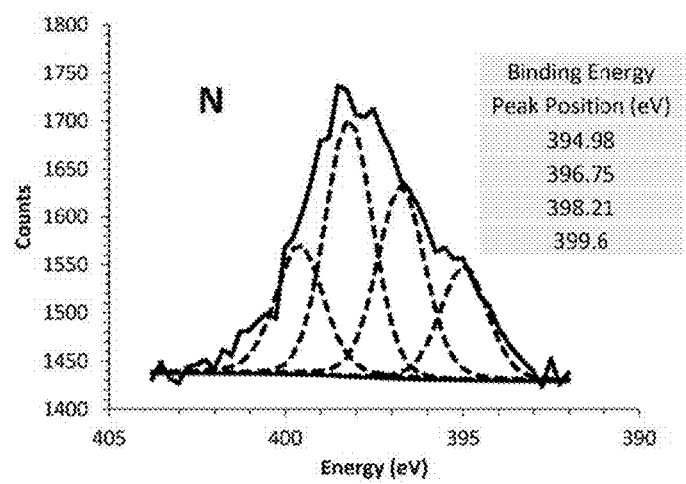
FIG. 7E is a nitrogen-region XPS of the LAERC of FIG. 7A.
Figure 7F:
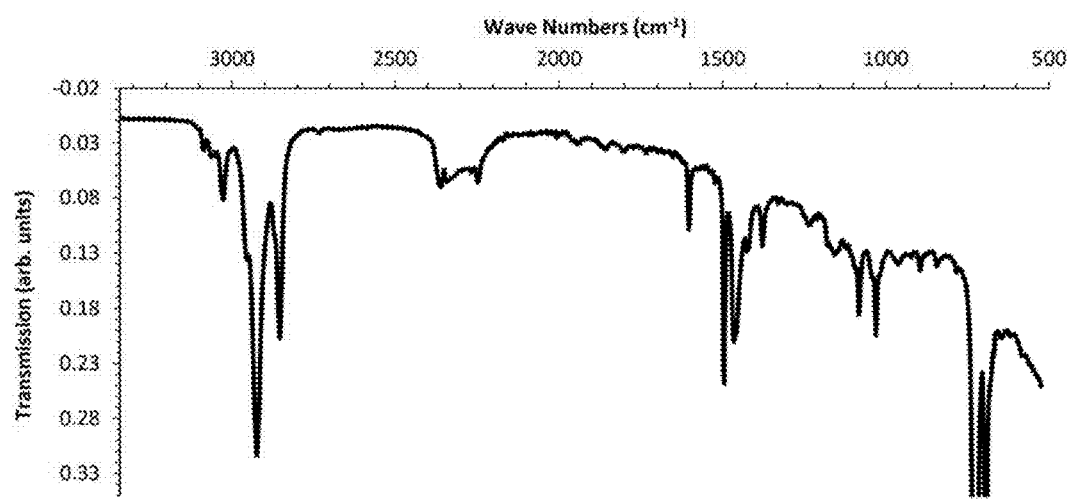
FIG. 7F is an FTIR of the LAERC of FIG. 7A.
Figure 8A:
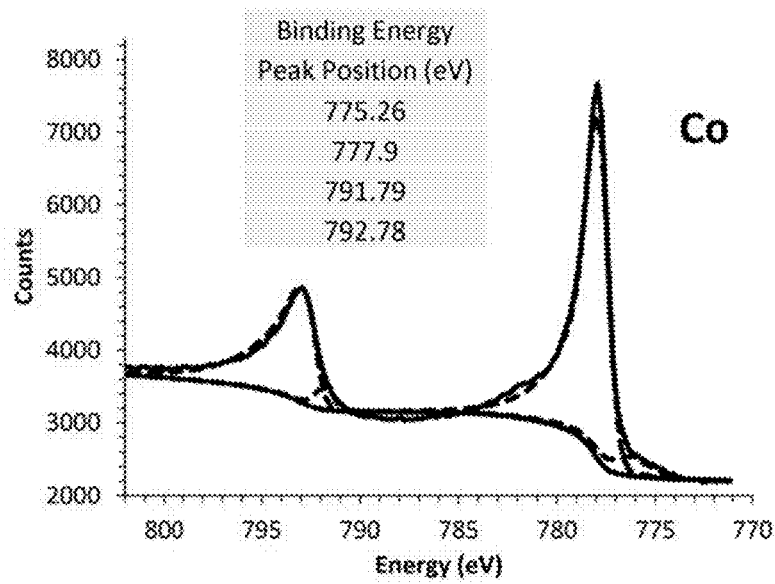
FIG. 8A is a cobalt-region XPS of a LAERC having the formula $Co(LiBH_4)_2(undecyl\ cyanide)_3$.
Figure 8B:
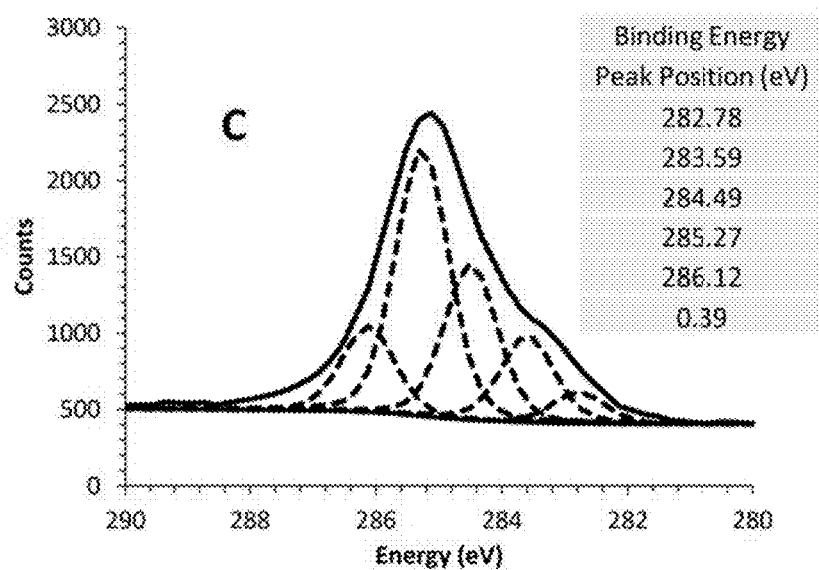
FIG. 8B is a carbon-region XPS of the LAERC of FIG. 8A.
Figure 8C:
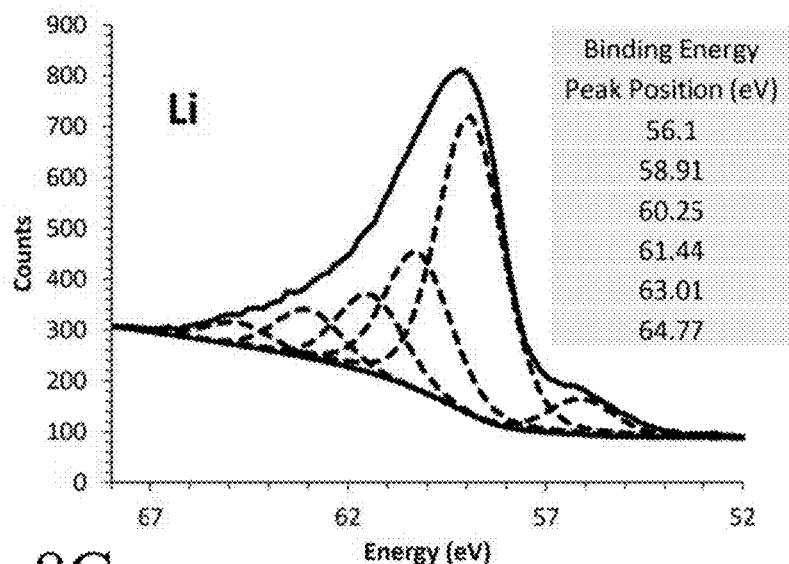
FIG. 8C is a lithium-region XPS of the LAERC of FIG. 8A.
Figure 8D:
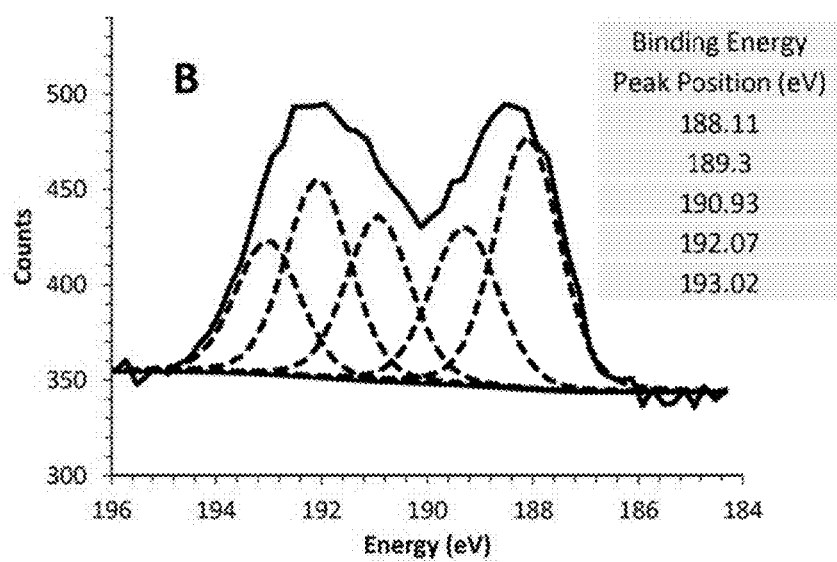
FIG. 8D is a boron-region XPS of the LAERC of FIG. 8A.
Figure 8E:
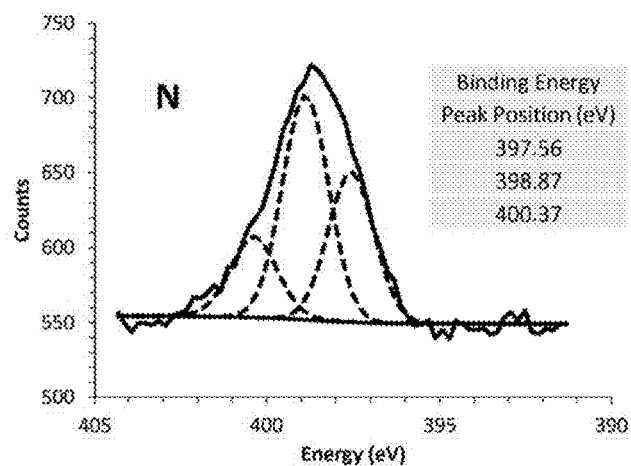
FIG. 8E is a nitrogen-region XPS of the LAERC of FIG. 8A.
Figure 8F:
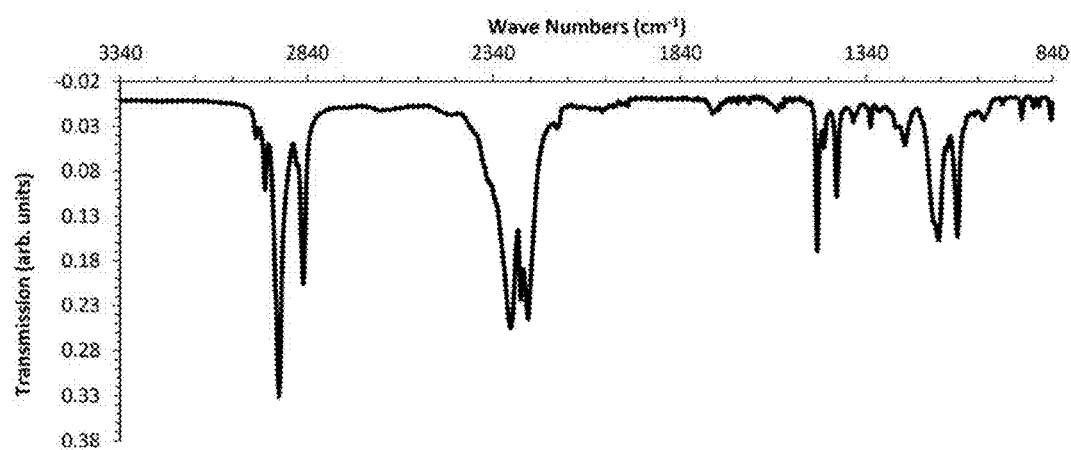
FIG. 8F is an FTIR of the LAERC of FIG. 8A.
Figure 9A:
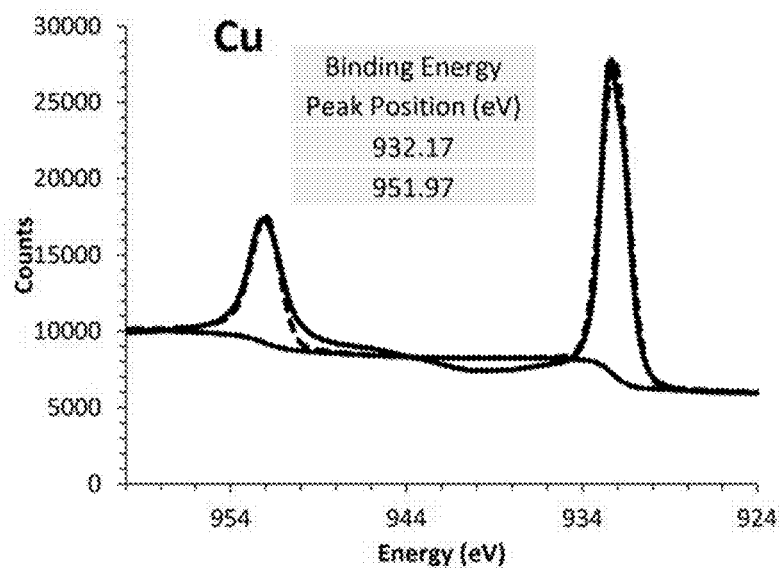
FIG. 9A is a copper-region XPS of a LAERC having the formula $Cu(LiBH_4)_2(undecyl\ cyanide)_3$.
Figure 9B:
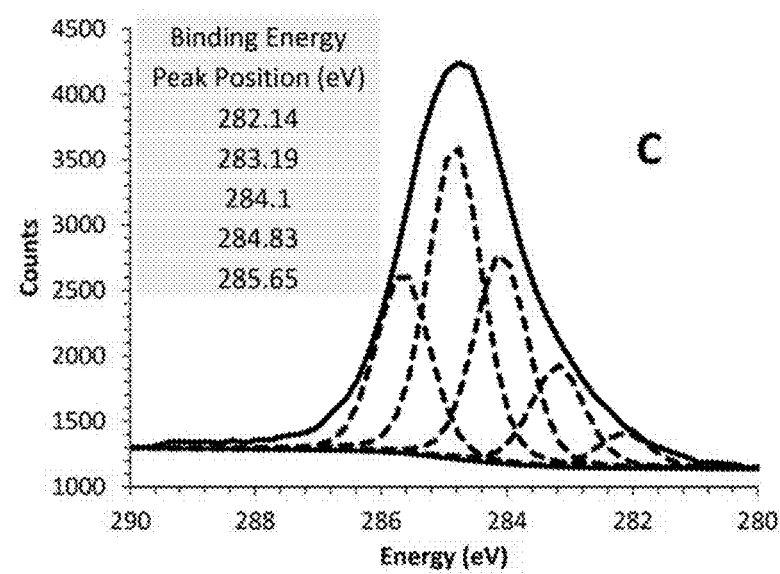
FIG. 9B is a carbon-region XPS of the LAERC of FIG. 9A.
Figure 9C:
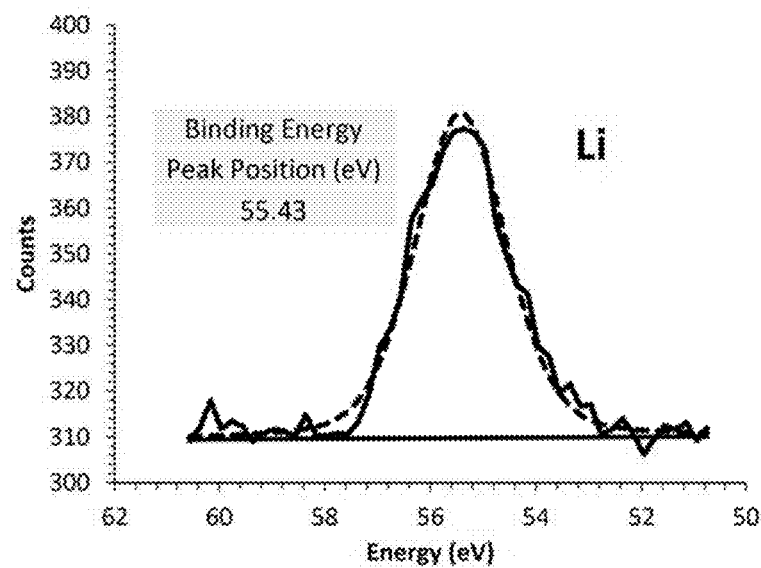
FIG. 9C is a lithium-region XPS of the LAERC of FIG. 9A.
Figure 9D:
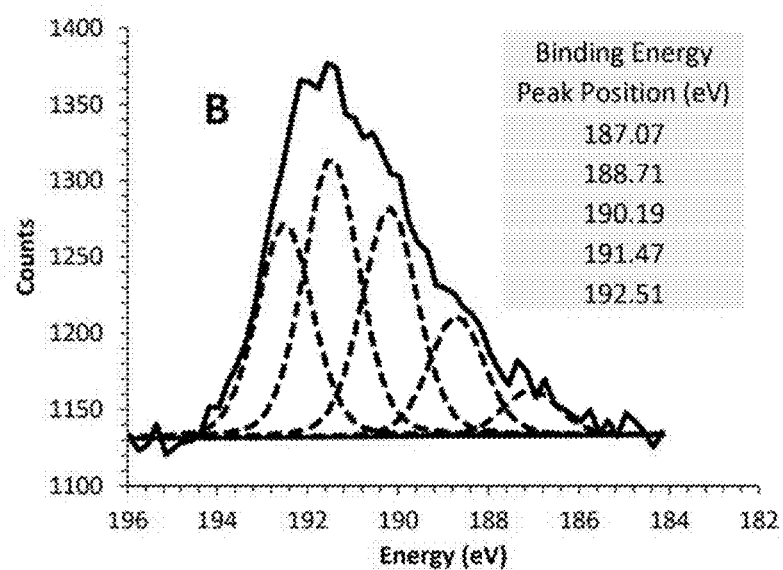
FIG. 9D is a boron-region XPS of the LAERC of FIG. 9A.
Figure 9E:
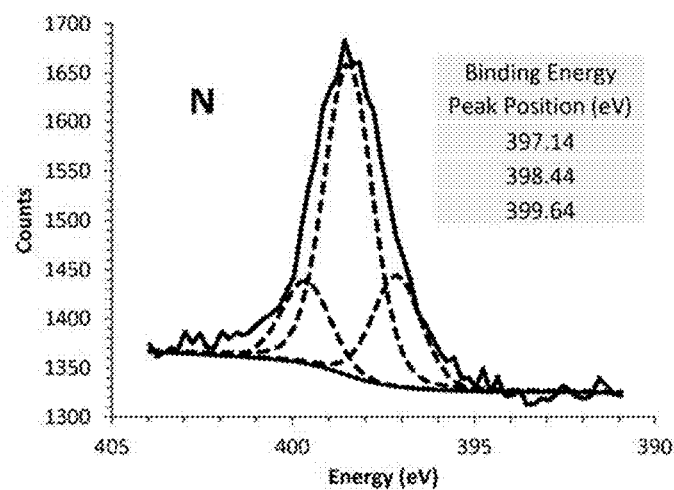
FIG. 9E is a nitrogen-region XPS of the LAERC of FIG. 9A.
Figure 9F:
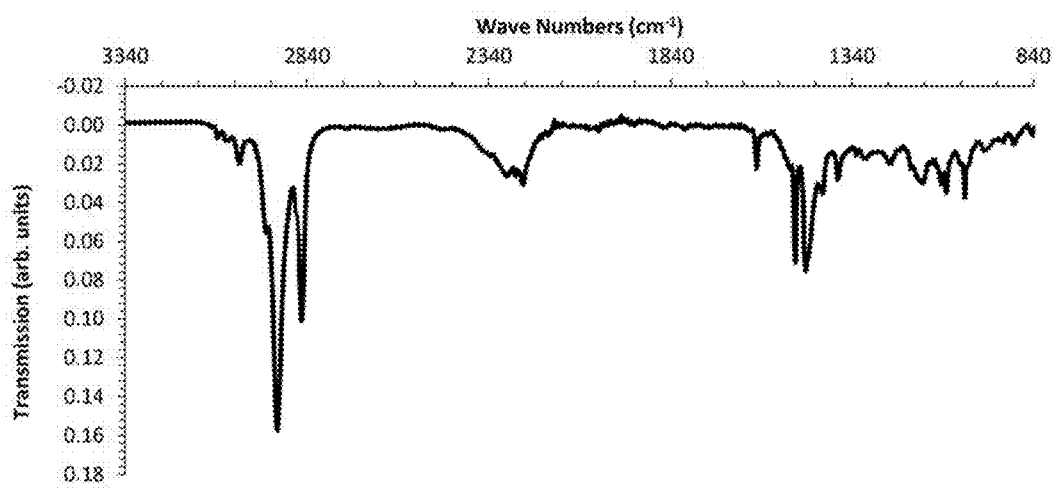
FIG. 9F is an FTIR of the LAERC of FIG. 9A.
Figure 10A:
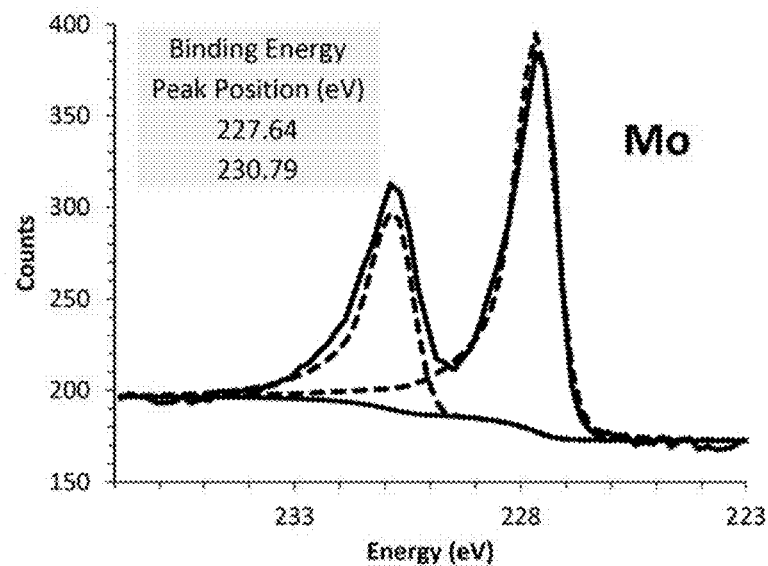
FIG. 10A is a molybdenum-region XPS of a LAERC having the formula $Mo(LiBH_4)_2(undecyl\ cyanide)_3$.
Figure 10B:
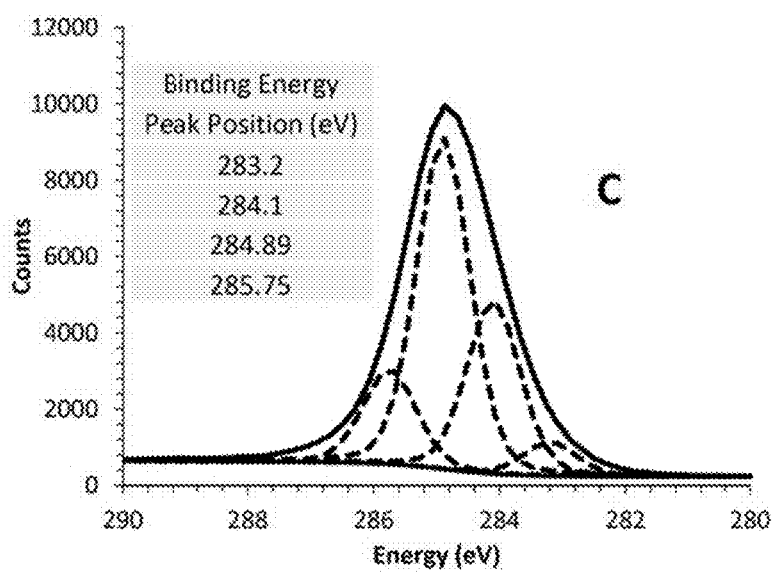
FIG. 10B is a carbon-region XPS of the LAERC of FIG. 10A.
Figure 10C:
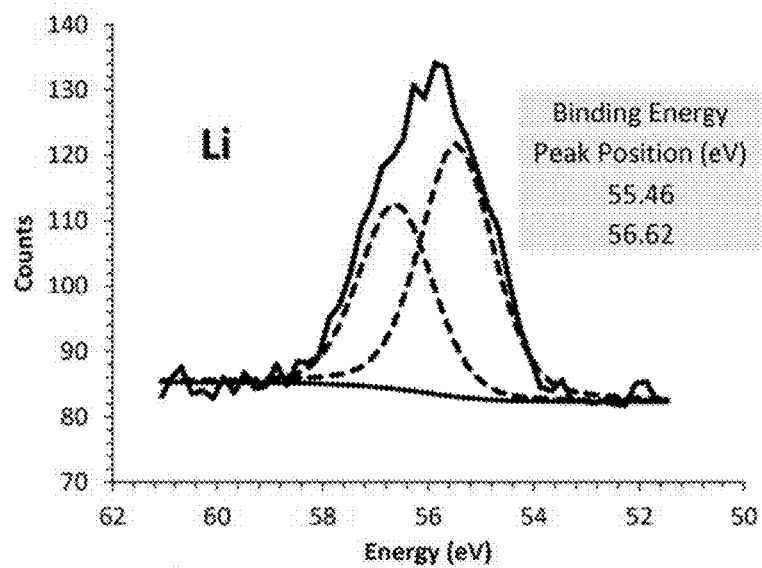
FIG. 10C is a lithium-region XPS of the LAERC of FIG. 10A.
Figure 10D:
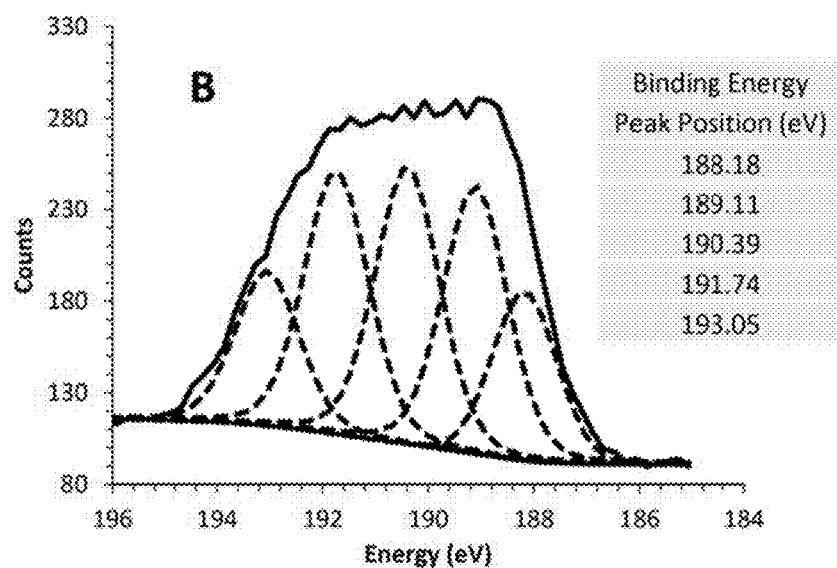
FIG. 10D is a boron-region XPS of the LAERC of FIG. 10A.
Figure 10E:
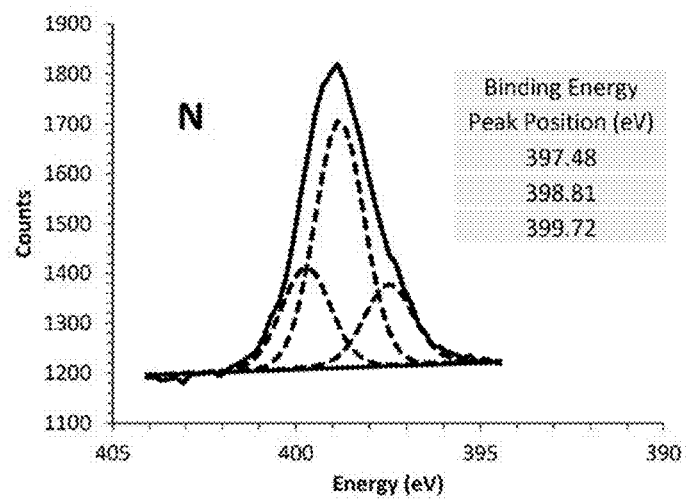
FIG. 10E is a nitrogen-region XPS of the LAERC of FIG. 10A.
Figure 10F:
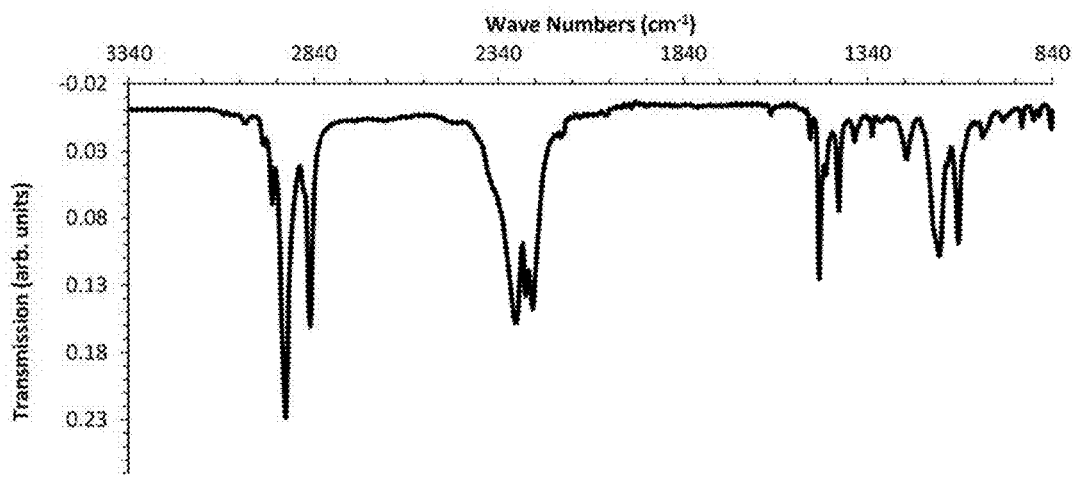
FIG. 10F is an FTIR of the LAERC of FIG. 10A.
Figure 11A:
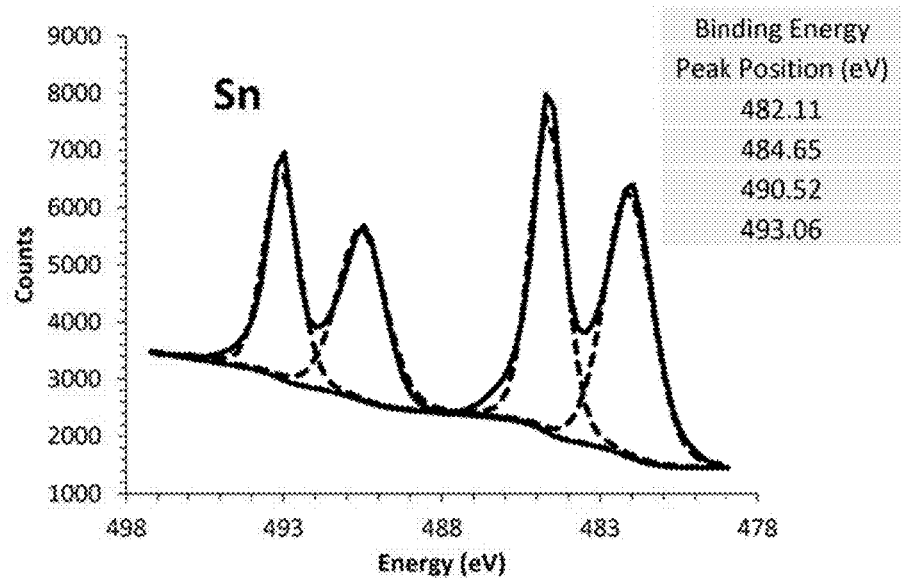
FIG. 11A is a tin-region XPS of a LAERC having the formula $Sn(LiBH_4)_2(undecyl\ cyanide)_3$.
Figure 11B:
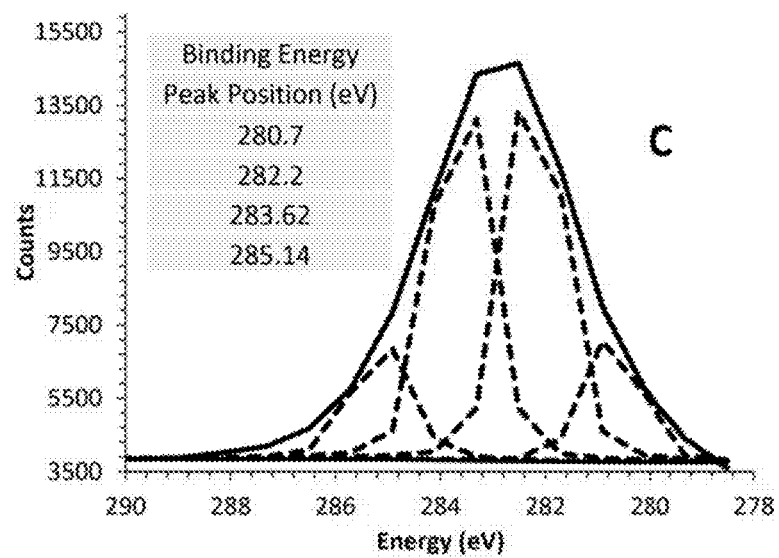
FIG. 11B is a carbon-region XPS of the LAERC of FIG. 11A.
Figure 11C:
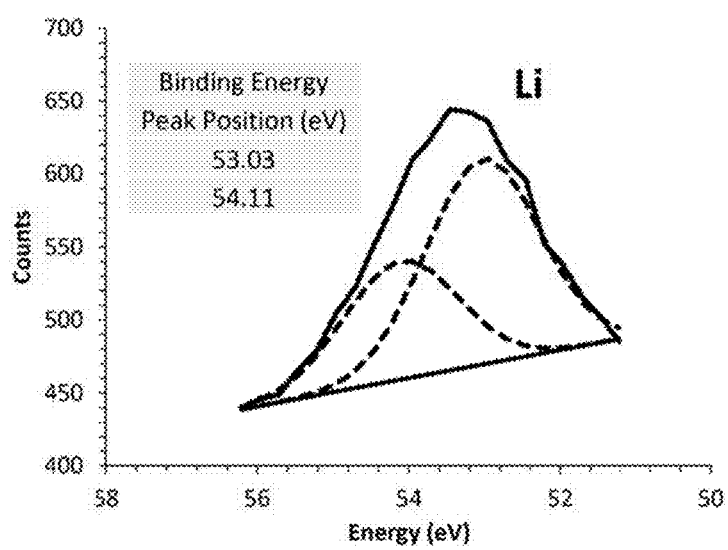
FIG. 11C is a lithium-region XPS of the LAERC of FIG. 11A.
Figure 11D:
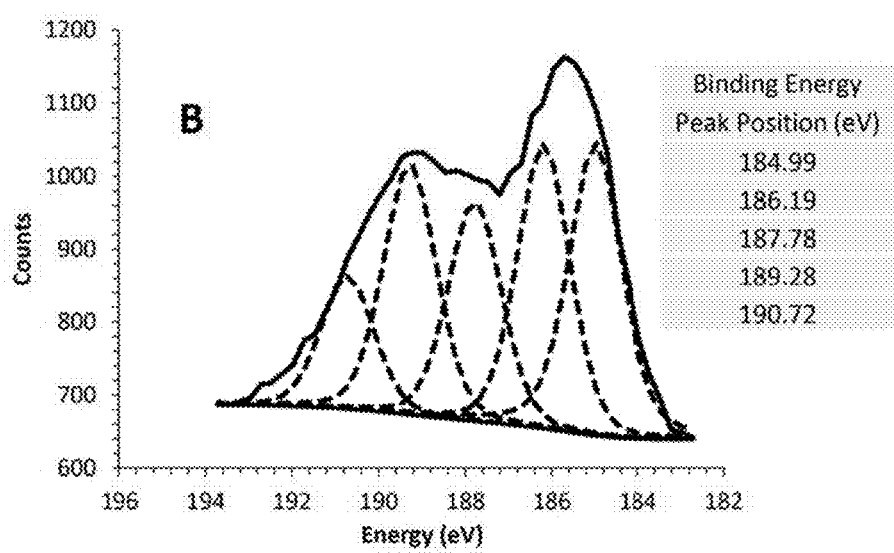
FIG. 11D is a boron-region XPS of the LAERC of FIG. 11A.
Figure 11E:
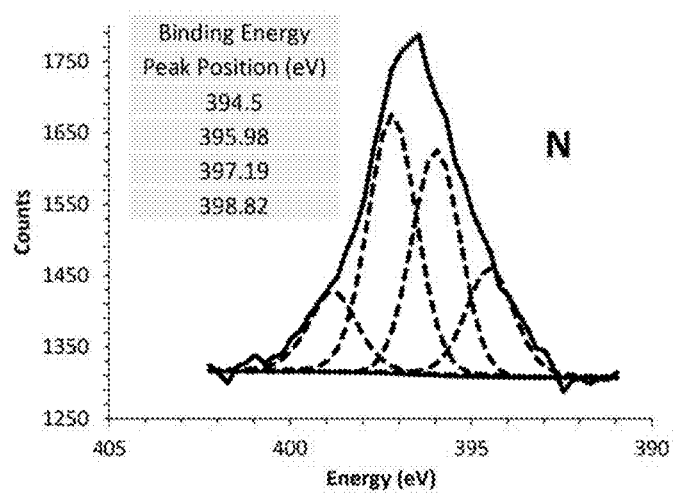
FIG. 11E is a nitrogen-region XPS of the LAERC of FIG. 11A.
Figure 11F:
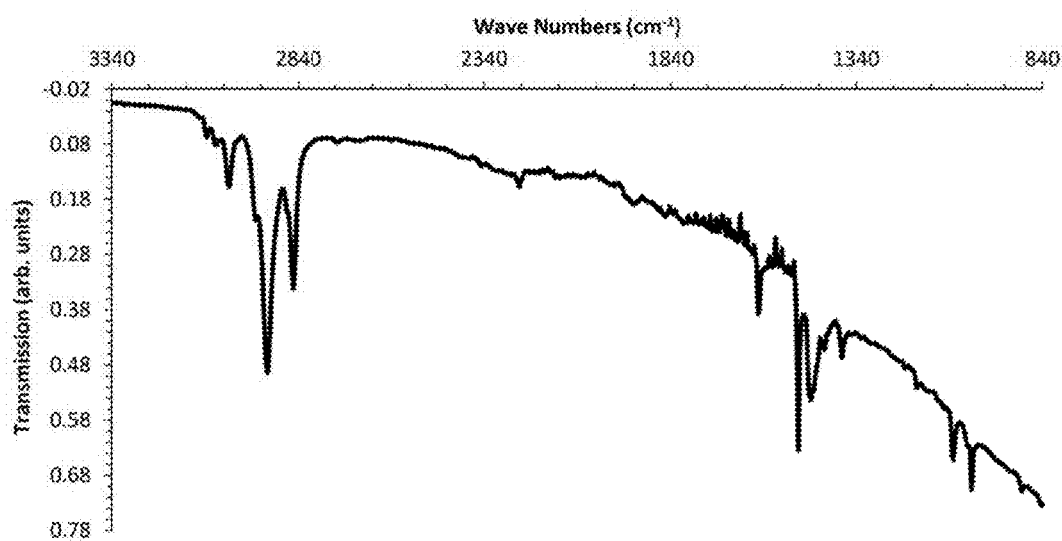
FIG. 11F is an FTIR of the LAERC of FIG. 11A.
Figure 12A:
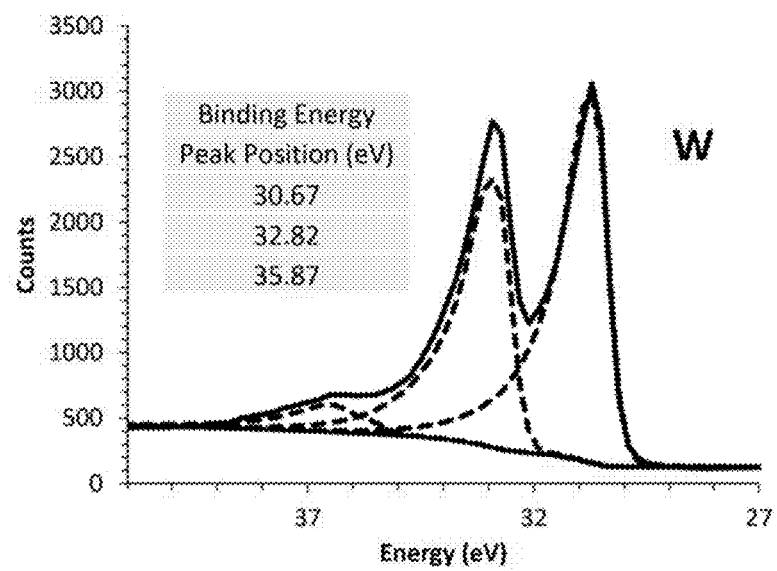
FIG. 12A is a tungsten-region XPS of a LAERC having the formula $W(LiBH_4)_2(undecyl\ cyanide)_3$.
Figure 12B:
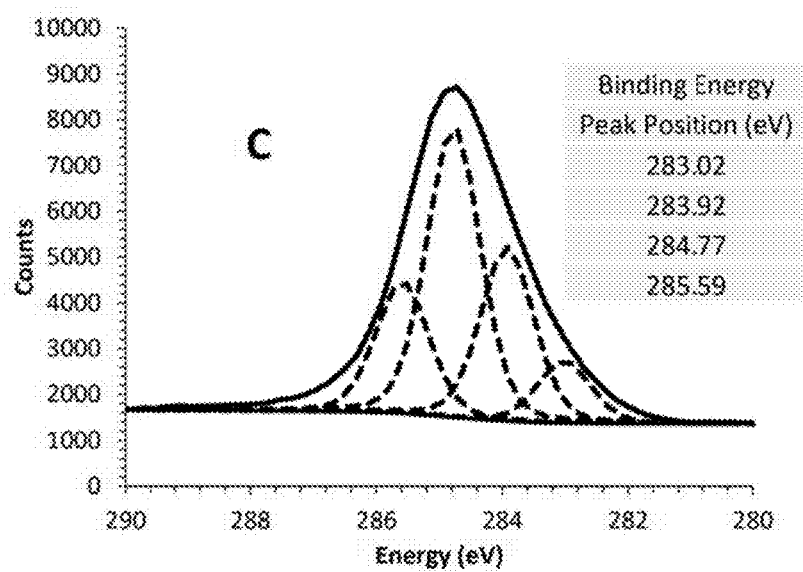
FIG. 12B is a carbon-region XPS of the LAERC of FIG. 12A.
Figure 12C:
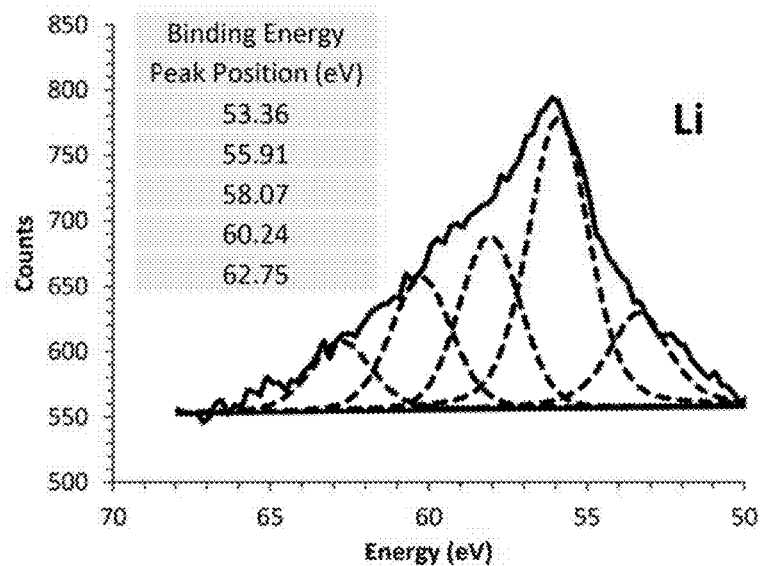
FIG. 12C is a lithium-region XPS of the LAERC of FIG. 12A.
Figure 12D:
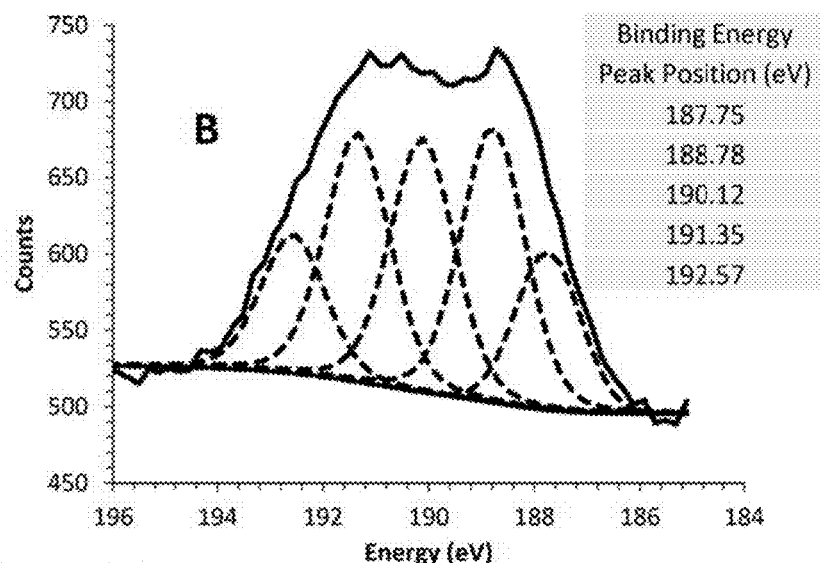
FIG. 12D is a boron-region XPS of the LAERC of FIG. 12A.
Figure 12E:
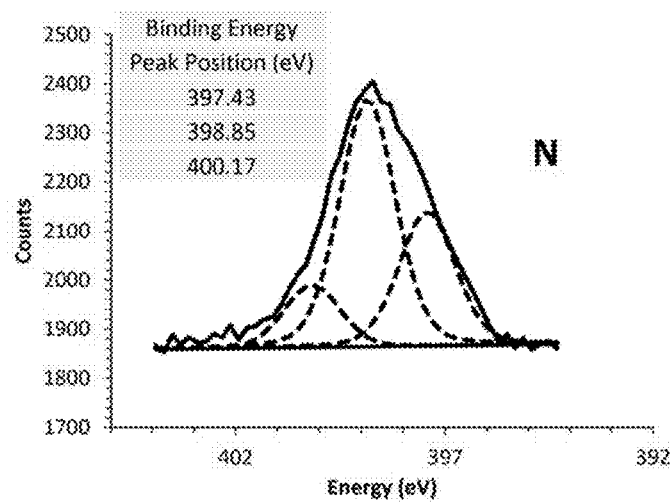
FIG. 12E is a nitrogen-region XPS of the LAERC of FIG. 12A.
Figure 12F:
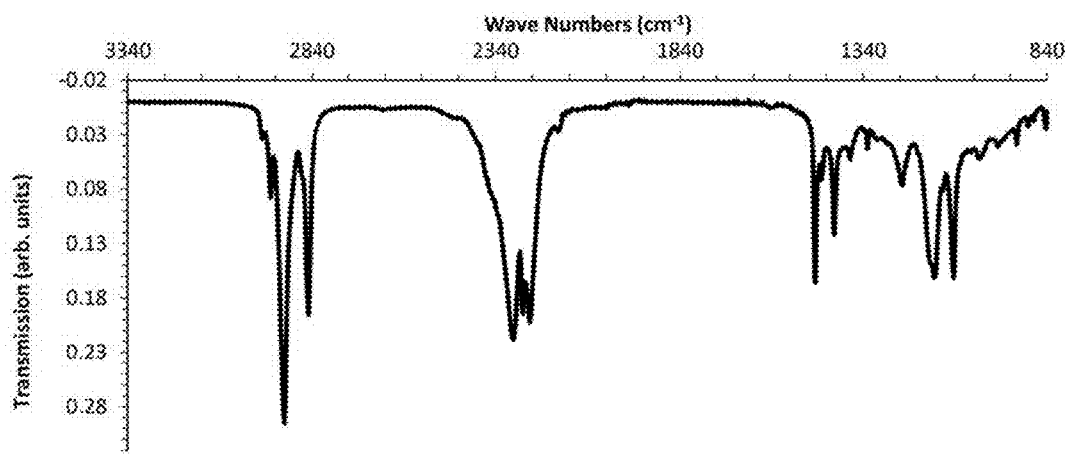
FIG. 12F is an FTIR of the LAERC of FIG. 12A.
Figure 13A:
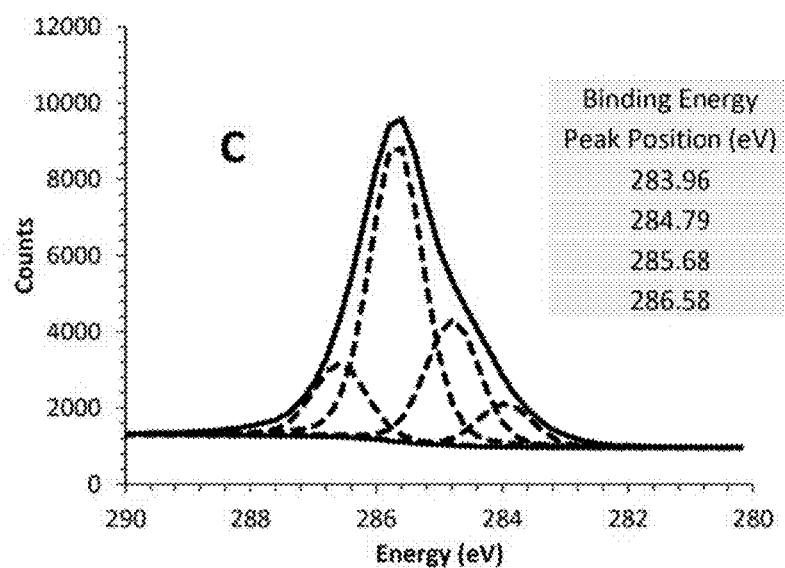
FIG. 13A is a carbon-region XPS of a LAERC having the formula $Se(LiBH_4)_2(undecyl\ cyanide)_3$.
Figure 13B:
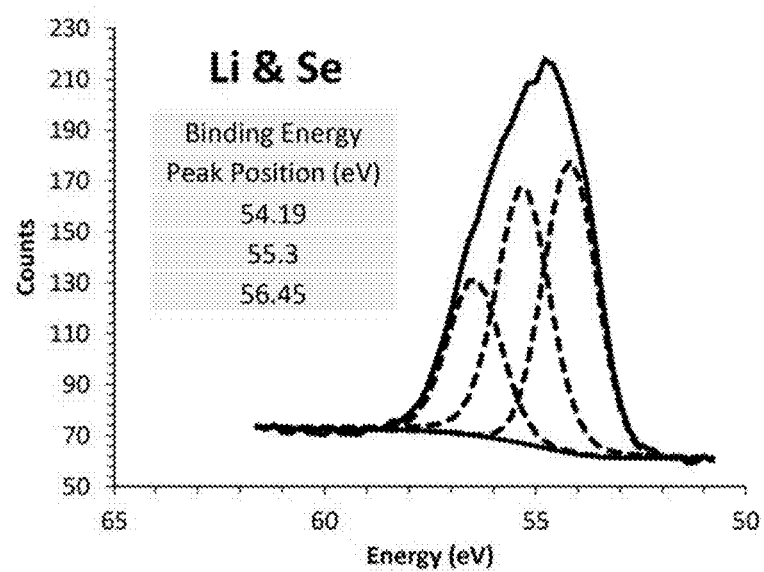
FIG. 13B is a lithium and selenium-region XPS of the LAERC of FIG. 13A.
Figure 13C:
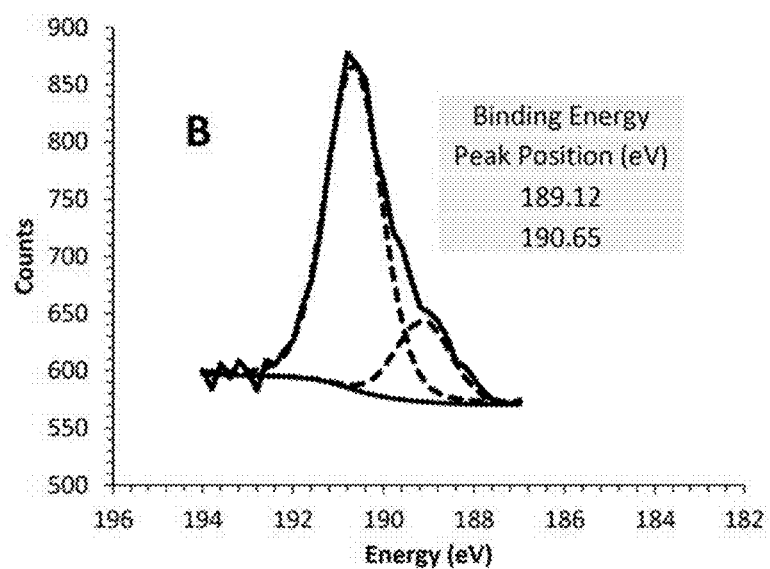
FIG. 13C is a boron-region XPS of the LAERC of FIG. 13A.
Figure 13D:
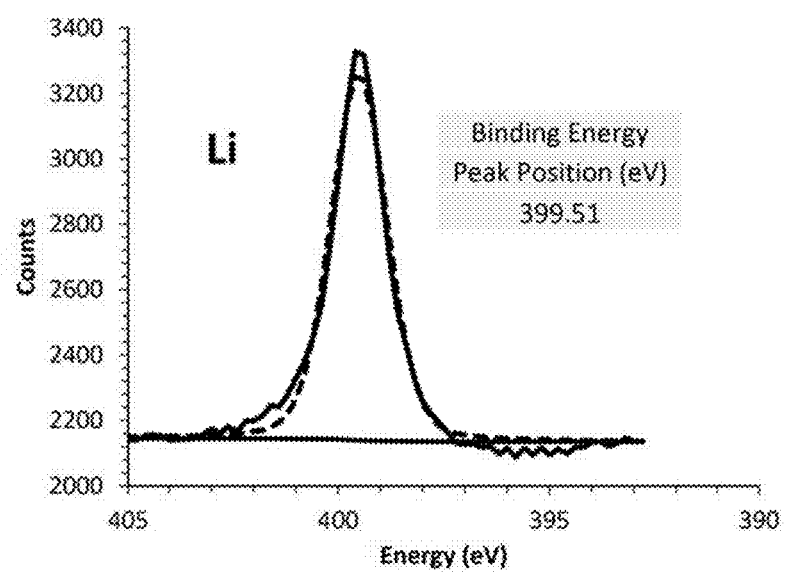
FIG. 13D is a lithium-region XPS of the LAERC of FIG. 13A.
Figure 13E:
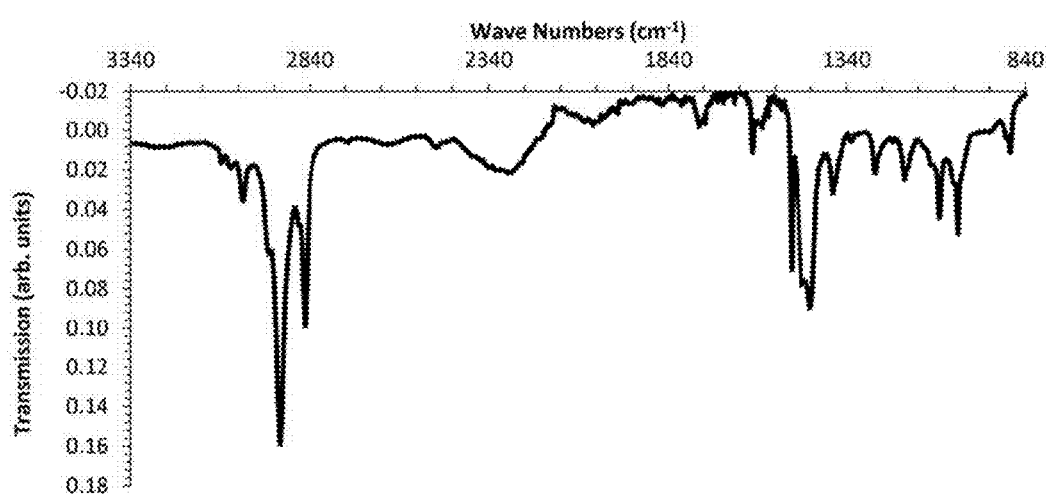
FIG. 13E is an FTIR of the LAERC of FIG. 13A.

As shown in FIG. 2E, successful LAERC formation is also observable by FT-IR. FIG. 2E shows offset overlays of FT-IR spectra of (i) bulk ligand (undecyl cyanide), (ii) bulk hydride molecule (lithium borohydride), and (iii) LAERC having elemental carbon in complex with lithium borohydride and incorporated undecyl cyanide. The FT-IR spectrum of the carbon LAERC shows a number of features absent from bulk ligand and bulk hydride molecule spectra, in particular a pair of relatively strong IR absorption bands located at about 1145 and 1155 $cm^{-1}$. This result is further indicative of successful LAERC formation, and suggests that complexation affects IR-active modes of the hydride molecule and/or incorporated ligand.

It is to be noted that the reagents of the present disclosure are suitable for the synthesis of nanoparticles containing the element, $Q^0$. For example, if $Q^0$ is a metal, $M^0$, and a second, cationic metal, $M'^+$, is added to the ligated reagent complex, the mixture can spontaneously form metal nanoparticles composed of an alloy of $M^0$ and $M'$, the metal $M'$ having been reduced to elemental form, i.e. to oxidation state zero.

The foregoing description is merely illustrative in nature and is in no way intended to limit the disclosure, its application, or uses. As used herein, the phrase at least one of A, B, and C should be construed to mean a logical (A or B or C), using a non-exclusive logical "or." It should be understood that the various steps within a method may be executed in different order without altering the principles of the present disclosure; various steps may be performed independently or at the same time unless otherwise noted. Disclosure of ranges includes disclosure of all ranges and subdivided ranges within the entire range.

The headings (such as "Background" and "Summary") and sub-headings used herein are intended only for general organization of topics within the present disclosure, and are not intended to limit the disclosure of the technology or any aspect thereof. The recitation of multiple embodiments having stated features is not intended to exclude other embodiments having additional features, or other embodiments incorporating different combinations of the stated features.

As used herein, the terms "comprise" and "include" and their variants are intended to be non-limiting, such that recitation of items in succession or a list is not to the exclusion of other like items that may also be useful in the devices and methods of this technology. Similarly, the terms "can" and "may" and their variants are intended to be non-limiting, such that recitation that an embodiment can or may comprise certain elements or features does not exclude other embodiments of the present technology that do not contain those elements or features.

The broad teachings of the present disclosure can be implemented in a variety of forms. Therefore, while this disclosure includes particular examples, the true scope of the disclosure should not be so limited since other modifications will become apparent to the skilled practitioner upon a study of the specification and the following claims. Reference herein to one aspect, or various aspects means that a particular feature, structure, or characteristic described in connection with an embodiment is included in at least one embodiment or aspect. The appearances of the phrase "in one aspect" (or variations thereof) are not necessarily referring to the same aspect or embodiment.

While particular embodiments have been described, alternatives, modifications, variations, improvements, and substantial equivalents that are or may be presently unforeseen may arise to applicants or others skilled in the art. Accordingly, the appended claims as filed and as they may be amended, are intended to embrace all such alternatives, modifications variations, improvements, and substantial equivalents.

What is claimed is:

1. A reagent comprising a complex having a formula:

$$Q^0 \cdot X_y L_z,$$

wherein:
Q$^0$ is an element in oxidation state zero selected from the group consisting of: carbon, phosphorous, sulfur, selenium, boron, silicon, germanium, arsenic, antimony, tellurium, polonium, a transition metal, an alkaline earth metal, and a lanthanide;
X is a hydride molecule selected from the group consisting of a complex metal hydride and a complex metalloid hydride;
L is a nitrile ligand;
y is an integral or fractional value greater than zero; and
z is an integral or fractional value greater than zero.

2. The reagent as recited in claim 1, wherein Q$^0$ is selected from the group consisting of: a transition metal, an alkaline earth metal, and a lanthanide.

3. The reagent as recited in claim 1, wherein $Q^0$ is selected from the group consisting of: boron, silicon, germanium, arsenic, antimony, tellurium, and polonium.

4. The reagent as recited in claim 1, wherein $Q^0$ comprises a non-metal is selected from the group consisting of: carbon, phosphorous, sulfur, and selenium.

5. The reagent as recited in claim 1, wherein X is lithium borohydride.

6. The reagent as recited in claim 1, wherein L is undecyl cyanide.

7. The reagent as recited in claim 1, wherein $Q^0$ is selected from the group consisting of boron, carbon, magnesium, titanium, manganese, iron, cobalt, copper, germanium, selenium, molybdenum, tin, and tungsten.

8. A method for synthesizing a reagent complex, comprising:
ball-milling a mixture that includes:
powder of an element in oxidation state zero selected from the group consisting of: carbon, phosphorous, sulfur, selenium, boron, silicon, germanium, arsenic, antimony, tellurium, polonium, a transition metal, an alkaline earth metal, and a lanthanide;
a bulk hydride molecule selected from the group consisting of a complex metal hydride and a complex metalloid hydride, and present at a first molar ratio relative to the powder of the element; and
a nitrile ligand present at a second molar ratio relative to the powder of the element;
wherein the ball-milling produces a complex having a formula:

$$Q^0 \cdot X_y L_z,$$

wherein $Q^0$ is the element, X is the hydride molecule, L is the nitrile ligand, y corresponds to the first molar ratio, and z corresponds to the second molar ratio.

9. The method as recited in claim 8, wherein the element is selected from the group consisting of: a transition metal, an alkaline earth metal, and a lanthanide.

10. The method as recited in claim 8, wherein the element is selected from the group consisting of: boron, silicon, germanium, arsenic, antimony, tellurium, and polonium.

11. The method as recited in claim 8, wherein the element is selected from the group consisting of: carbon, phosphorous, sulfur, and selenium.

12. The method as recited in claim 8, wherein the element is selected from the group consisting of boron, carbon, magnesium, titanium, manganese, iron, cobalt, copper, germanium, selenium, molybdenum, tin, and tungsten.

13. The method as recited in claim 8, wherein the bulk hydride molecule is lithium borohydride.

14. The method as recited in claim 8, wherein the nitrile ligand is undecyl cyanide.

* * * * *